us009310354B2

United States Patent
Duncan et al.

(10) Patent No.: US 9,310,354 B2
(45) Date of Patent: *Apr. 12, 2016

(54) METHODS OF PREDICTING CROP YIELD USING METABOLIC PROFILING

(75) Inventors: Kateri Duncan, West Des Moines, IA (US); Jonathan Cohn, Research Triangle Park, NC (US); Lining Guo, Chapel Hill, NC (US); Nalini Desai, Chapel Hill, NC (US); Matthew Mitchell, Durham, NC (US); Jacob Wulff, Morrisville, NC (US)

(73) Assignee: Syngenta Participations AG, Basel (CH)

( * ) Notice: Subject to any disclaimer, the term of this patent is extended or adjusted under 35 U.S.C. 154(b) by 87 days.

This patent is subject to a terminal disclaimer.

(21) Appl. No.: 14/002,250

(22) PCT Filed: Mar. 7, 2012

(86) PCT No.: PCT/US2012/027944
§ 371 (c)(1),
(2), (4) Date: Aug. 29, 2013

(87) PCT Pub. No.: WO2012/122199
PCT Pub. Date: Sep. 13, 2012

(65) Prior Publication Data
US 2014/0189903 A1    Jul. 3, 2014

Related U.S. Application Data

(60) Provisional application No. 61/450,033, filed on Mar. 7, 2011.

(51) Int. Cl.
*G01N 33/50* (2006.01)
*A01H 1/04* (2006.01)
*G01N 33/48* (2006.01)
*G06G 7/75* (2006.01)
*A01C 21/00* (2006.01)

(52) U.S. Cl.
CPC .......... *G01N 33/5097* (2013.01); *A01C 21/007* (2013.01); *A01H 1/04* (2013.01); *G01N 33/48* (2013.01); *G01N 33/5038* (2013.01); *G06G 7/75* (2013.01)

(58) Field of Classification Search
CPC .......... G01N 33/5038; G01N 33/5097; G01N 33/48; G06G 7/75
USPC .................. 800/260, 266, 267; 702/19; 703/2
See application file for complete search history.

(56) References Cited

U.S. PATENT DOCUMENTS

| 7,105,654 | B1 | 9/2006 | Nelson |
| 2006/0064772 | A1 | 3/2006 | Kriz et al. |
| 2007/0089180 | A1 | 4/2007 | Glazebrook et al. |
| 2007/0231864 | A1 | 10/2007 | Havkin-Frenkel et al. |
| 2008/0115240 | A1 | 5/2008 | Aukerman et al. |
| 2009/0070898 | A1 | 3/2009 | Allen et al. |
| 2009/0193543 | A1 | 7/2009 | Sanz Molinero et al. |
| 2009/0235392 | A1 | 9/2009 | Meister et al. |
| 2010/0145625 | A1* | 6/2010 | Altmann et al. ............... 702/19 |
| 2010/0242135 | A1 | 9/2010 | Qiao et al. |
| 2013/0139277 | A1 | 5/2013 | Tierney |

OTHER PUBLICATIONS

Seebauer et al., "Amino Acid Metabolism in Maize Earshoots. Implications for Assimilate Preconditioning and Nitrogen Signalling." Plant Physiology, Dec. 2004, vol. 136, pp. 4326-4334.*
Steinfath et al., "Discovering Plant Metabolic Biomarkers for Phenotype Prediction Using an Untargeted Approach," Plant Biotechnology Journal (2010) 8, pp. 900-911.*
Seebauer et al., "Amino Acid Metabolism in Maize Earshoots. Implications for Assimilate Preconditioning and Nitrogen Signaling," Plant Physiology, Dec. 2004, vol. 136, p. 4326-4334.
Zhang et al., "Review: Nutrient Loading of Developing Seeds," Functional Plant Biology, 2007, 34; p. 314-331.
Howarth et al., "Co-ordinated Expression of Amino Acid Metabolism in Response to N and S Deficiency During Wheat Grain Filling," Journal of Experimental Botany, 2008, vol. 59, No. 13, p. 3675-3689.
Basso et al., "Review of Crop Yield Forecasting Methods and Early Warning Systems," http://www.fao.org/fileadmin/templates/ess/documents/meetings_and_workshops/GS_SAC_2013/Improving_methods_for_crops_estimates/Crop_Yield_Forecasting_Methods_and_Early_Warning_Systems_Lit_review.pdf (2013).
International Search Report and Written Opinion for PCT/US2012/027944 dated Jun. 1, 2012.

* cited by examiner

*Primary Examiner* — Anne Grunberg
(74) *Attorney, Agent, or Firm* — Karen Moon Bruce

(57) ABSTRACT

The present invention relates to the fields of agriculture, plant breeding or genetic engineering for plants with increased yield, crop forecasting and crop management. In particular, the methods herein describe novel methods of predicting a plant's yield through the measurement of specific metabolites either individually or in combination with one another in a specific plant reproductive tissue. The plant predictive methods described herein may be used to predict yield of plant populations as well as allow for more efficient crop management practices (e.g. amount and timing of chemical applications or amount of irrigation water applied to a field).

36 Claims, No Drawings

SEQUENCE LISTING

```
<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Phe, Tyr, Trp or Leu
<220> FEATURE:
<221> NAME/KEY: MISC_FEATURE
<222> LOCATION: (6)..(11)
<223> OTHER INFORMATION: Xaa is any naturally occurring amino acid
<220> FEATURE:
<221> NAME/KEY: MISC_FEATURE
<222> LOCATION: (12)..(12)
<223> OTHER INFORMATION: Xaa is Asp, Glu, Asn, Gln, Ser, Thr, Ala or Lys
<220> FEATURE:
<221> NAME/KEY: MISC_FEATURE
<222> LOCATION: (13)..(13)
```

```
<223> OTHER INFORMATION: Xaa is Ser or Ala
<220> FEATURE:
<221> NAME/KEY: MISC_FEATURE
<222> LOCATION: (14)..(14)
<223> OTHER INFORMATION: Xaa is Asp or Glu
<220> FEATURE:
<221> NAME/KEY: MISC_FEATURE
<222> LOCATION: (15)..(16)
<223> OTHER INFORMATION: Xaa is any naturally occurring amino acid
<220> FEATURE:
<221> NAME/KEY: MISC_FEATURE
<222> LOCATION: (17)..(17)
<223> OTHER INFORMATION: Xaa is Leu, Ile, Val, Met, Phe or Tyr

<400> SEQUENCE: 1

Xaa Asp Gly Ser Ser Xaa Xaa Xaa Xaa Xaa Xaa Xaa Xaa Xaa Xaa
1               5                   10                  15

Xaa

<210> SEQ ID NO 2
<211> LENGTH: 18
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Phe, Tyr, Trp or Leu
<220> FEATURE:
<221> NAME/KEY: MISC_FEATURE
<222> LOCATION: (6)..(12)
<223> OTHER INFORMATION: Xaa is any naturally occurring amino acid
<220> FEATURE:
<221> NAME/KEY: MISC_FEATURE
<222> LOCATION: (13)..(13)
<223> OTHER INFORMATION: Xaa is Asp, Glu, Asn, Gln, Ser, Thr, Ala or Lys
<220> FEATURE:
<221> NAME/KEY: MISC_FEATURE
<222> LOCATION: (14)..(14)
<223> OTHER INFORMATION: Xaa is Ser or Ala
<220> FEATURE:
<221> NAME/KEY: MISC_FEATURE
<222> LOCATION: (15)..(15)
<223> OTHER INFORMATION: Xaa is Asp or Glu
<220> FEATURE:
<221> NAME/KEY: MISC_FEATURE
<222> LOCATION: (16)..(17)
<223> OTHER INFORMATION: Xaa is any naturally occurring amino acid
<220> FEATURE:
<221> NAME/KEY: MISC_FEATURE
<222> LOCATION: (18)..(18)
<223> OTHER INFORMATION: Xaa is Leu, Ile, Val, Met, Phe or Tyr

<400> SEQUENCE: 2

Xaa Asp Gly Ser Ser Xaa Xaa Xaa Xaa Xaa Xaa Xaa Xaa Xaa Xaa
1               5                   10                  15

Xaa Xaa

<210> SEQ ID NO 3
<211> LENGTH: 19
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Phe, Tyr, Trp or Leu
<220> FEATURE:
<221> NAME/KEY: MISC_FEATURE
<222> LOCATION: (6)..(13)
<223> OTHER INFORMATION: Xaa is any naturally occurring amino acid
```

```
-continued

<220> FEATURE:
<221> NAME/KEY: MISC_FEATURE
<222> LOCATION: (14)..(14)
<223> OTHER INFORMATION: Xaa is Asp, Glu, Asn, Gln, Ser, Thr, Ala or Lys
<220> FEATURE:
<221> NAME/KEY: MISC_FEATURE
<222> LOCATION: (15)..(15)
<223> OTHER INFORMATION: Xaa is Ser or Ala
<220> FEATURE:
<221> NAME/KEY: MISC_FEATURE
<222> LOCATION: (16)..(16)
<223> OTHER INFORMATION: Xaa is Asp or Glu
<220> FEATURE:
<221> NAME/KEY: MISC_FEATURE
<222> LOCATION: (17)..(18)
<223> OTHER INFORMATION: Xaa is any naturally occurring amino acid
<220> FEATURE:
<221> NAME/KEY: MISC_FEATURE
<222> LOCATION: (19)..(19)
<223> OTHER INFORMATION: Xaa is Leu, Ile, Val, Met, Phe or Tyr

<400> SEQUENCE: 3

Xaa Asp Gly Ser Ser Xaa Xaa Xaa Xaa Xaa Xaa Xaa Xaa Xaa Xaa
1               5                   10                  15

Xaa Xaa Xaa

<210> SEQ ID NO 4
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is any naturally occurring amino acid
<220> FEATURE:
<221> NAME/KEY: MISC_FEATURE
<222> LOCATION: (4)..(5)
<223> OTHER INFORMATION: Xaa is any naturally occurring amino acid

<400> SEQUENCE: 4

Gly Xaa Gly Xaa Xaa Gly
1               5
```

METHODS OF PREDICTING CROP YIELD USING METABOLIC PROFILING

FIELD OF THE INVENTION

The present invention relates to the fields of agriculture, plant breeding or genetic engineering for plants with increased yield, crop forecasting and crop management. In particular, the methods herein describe novel methods of predicting a plant's yield through the measurement of specific metabolites either individually or in combination with one another in a specific plant reproductive tissue. The plant predictive methods described herein may be used to predict yield of plant populations as well as allow for more efficient crop management practices (e.g. amount and timing of chemical applications or amount of irrigation water applied to a field). These and more utilities enabled by the novel predictive methods described herein are described in further detail herein.

STATEMENT REGARDING ELECTRONIC SUBMISSION OF A SEQUENCE LISTING

A Sequence Listing in ASCII text format, submitted under 37 C.F.R. §1.821, entitled 73051 US REG ORG P 1 07FEB2014 SeqListing ST25.txt, 4 KB in size, generated on Feb. 07, 2014 and filed via EFS-Web is provided in lieu of a paper copy. This Sequence Listing is hereby incorporated by reference into the specification for its disclosure.

BACKGROUND OF THE INVENTION

Plant yield is a very complex trait involving on a molecular basis the interaction of many pathways and interacting factors. There has been a tremendous amount of focus in the field of commercial agriculture over the past decade to develop higher yielding plants either through traditional plant breeding or genetic modifications. In a simplified view, the yield of a plant ultimately depends on the energy the plant gains through fixing carbon dioxide into carbohydrates during photosynthesis. The primary plant tissue involved in photosynthesis are the leaves and to a lesser extent the stem tissue. All other tissues such as the roots and seed are dependent on the photoassimilates made in the photosynthetic tissue. In general, this can be seen as an energy flow from photosynthetically active tissues to photosynthetically inactive tissues.

Phloem transport of this energy is determined by the relative locations of the areas of supply and utilization of the products of photosynthesis. Translocation occurs from areas of supply (sources) to areas of metabolism of storage (sinks). Sources include any exporting organ, typically a mature leaf that is capable of producing photosynthate in excess of its own needs. The direction of phloem transport of this energy is determined by the relative locations of the areas of supply and utilization of the products of photosynthesis. Another type of source is a storage organ during the exporting phase of its development. For example, a storage root may be a sink during the first growing season when it accumulates sugars received from the source leaves. During the second growing season the same root could become a source, when the stored sugars are remobilized and utilized to produce a new shoot which ultimately becomes reproductive. Sinks include any non-photosynthetic organs of the plant and organs that do not produce enough photosynthetic products to support their own growth or storage needs. Roots, tubers, developing fruits and immature leaves which must import carbohydrate for normal development are all examples of sink tissues. Sink tissues differ in their ability to attract source products. Elements such as stress, developmental stages of plant tissues, and osmotic potential all may affect the transport of photoassimilates.

Differential distribution of photoassimilates within the plant is termed partitioning. Partitioning of assimilated carbon amongst sink organs is a critical factor that controls rate and pattern of plant growth. The regulation of the diversion of fixed carbon into the various metabolic pathways is termed allocation. The rate of fixed carbon in a source cell can be classified into three principle categories; storage, utilization, and transport. Starch is synthesized and stored within chloroplasts and in most species is a primary storage form that is mobilized for translocation during the night. Fixed carbon can be utilized within various compartments of the photosynthesizing cell to meet energy needs of the cell or provide carbon skeletons for the synthesis of other compounds required by the cells. Fixed carbon can also be incorporated into transport sugars for export to various sink tissues.

The rate of photosynthesis of leaves is strongly influenced by the demands of the sink. There are cases in which senescent leaves can be rejuvenated to full photosynthetic performance when the sink/source ratio is increased substantially. On the other hand rapid growth of a sink can sometimes compete with leaves for remobilizable nitrogen leading to senescence of the leaf and a drop in its photosynthetic capacity. Young leaves normally act as a sink rather than as a source. After a certain time however they begin to export carbohydrates to the phloem although import carbohydrate may continue for a while through different vascular strands. Once sucrose begins to actively load into companion cells and then into the sieve elements, water will enter by osmosis and flow will begin out of the line of veins. The leaf will become a source instead of a sink.

Two primary photoassimilates are sugar and starch, and these products are important to yield and plant development. Sugar and starch biochemistry are interrelated in plants. (See, e.g., Sivak, M. N. and J. Preiss (1994). Starch synthesis in seeds. In: Seed development and germination. Kigel, J. and G. Galili, eds. (Marcel Dekker, New York), pp. 139-168; J. S. Hawker (1985). Sucrose. In: Biochemistry of storage carbohydrates in green plants. P. M. Dey and R. A. Dixon, Eds., (Academic Press, London), pp. 1-51, which are incorporated herein by reference).

During the early development of storage organs, such as seeds and tubers, sucrose is imported and used for building the cellular components required for growth and development. Following this phase the metabolic program changes to convert the imported sucrose into storage compounds such as starch in tubers and fatty acids in oil seeds. Metabolism is finally altered to convert the starch and oils into reduced carbon compounds for the development of sprouts and seedlings respectively. Sucrose levels rise when hexoses decrease apparently terminating cell division in initiating differentiation and storage activities.

Early ear development in species belonging to the grass family Poaceae (e.g. wheat, maize, wheat, etc) relies upon concurrent photosynthate transport into reproductive sink tissue, as the developing seed cannot utilize stored photoassimilates present in other plant tissues. Because the seed are weak sinks, it is unable to attract stored reserves from source tissues. Seed abortion may occur when concurrent photosynthate is insufficient to meet the needs of reproductive growth, resulting in dramatically decreased yield, or in the case of maize ear, barrenness. Anthesis is generally recognized as the critical period of ear and kernel development. Varied experimental approaches have demonstrated that treatments, which decrease the plant carbon exchange rate (CER) around anthesis, decrease grain yield. For example, large yield losses occur when maize plants are shaded (Early et al., 1967; Schussler and Westgate, 1991; Andrade et al., 1993), defoliated (Tollenaar and Daynard, 1978), subjected to water-deficits (Denmead and Shaw, 1960; Claassen and Shaw, 1970; Moss and Downey, 1971; Westgate and Boyer, 1986; Schussler and Westgate, 1991) or exposed to high plant density (Prine, 1971; Baenziger and Glover, 1980) around anthesis. Conversely, treatments that increase plant CER around anthesis increase grain yield. For example, yield enhancements are obtained when maize plants are provided supplemental radiation (Schoper et al., 1982; Ottman and Welch, 1988). In all cases, the variation in yield was directly related to the number of kernels that developed and supply of concurrent photosynthate. Collectively, these results suggest that kernel number may be limited by carbohydrate supply, particularly during drought stress at anthesis.

One aspect that has not been looked at in detail, is whether or not metabolic profiling in these source and/or sink tissues may give insight into the more subtle processes such as sugar and stress signaling. Metabolic profiling has become a powerful tool in the discovery of processes, interactions, compounds and pathways that might be involved in various biological phenomena. According to the invention, further exploration into metabolite profiling of reproductive sink tissue has led to some unexpected findings that certain metabolite profiles can be utilized to make a determination as to predicting yield of an individual plant. Accordingly, data from single plants can be further statistically validated to predict the yield of a given plant population. The ability to correlate yield with the presence or absence of specific metabolites and/or combinations thereof in reproductive sink tissue have many useful applications that will be described further herein.

SUMMARY OF THE INVENTION

The methods herein provide novel methods of predicting a plant's yield through the measurement of specific metabolites either individually or in combination with one another in a specific plant reproductive sink tissue. The plant predictive methods described herein may be used to predict yield of plant populations as well as allow for more efficient crop management practices (e.g. amount and timing of chemical applications or amount of irrigation water applied to a field).

Further provided are methods of utilizing the yield predictive methods described herein to develop plant breeding programs, identify genes and/or metabolic pathways associated with plant yield, and derive fast plant evaluation methods to select for high yielding lines.

These and other features, objects and advantages of the present invention will become better understood from the description that follows. The description of preferred embodiments is not intended to limit the invention to cover all modifications, equivalents and alternatives. Reference should therefore be made to the embodiments recited herein for interpreting the scope of the invention.

DEFINITIONS

The practice of the present invention will employ, unless otherwise indicated, conventional techniques of botany, microbiology, tissue culture, molecular biology, chemistry, biochemistry, plant quantitative genetics, statistics and recombinant DNA technology, which are within the skill of the art. Such techniques are explained fully in the literature. See, e.g., Langenheim and Thimann, (1982) Botany: Plant Biology and Its Relation to Human Affairs, John Wiley; Cell Culture and Somatic Cell Genetics of Plants, vol. 1, Vasil, ed. (1984); Stanier, et al., (1986) The Microbial World, 5th ed., Prentice-Hall; Dhringra and Sinclair, (1985) Basic Plant Pathology Methods, CRC Press; Maniatis, et al., (1982) Molecular Cloning: A Laboratory Manual; DNA Cloning, vols. I and II, Glover, ed. (1985); Oligonucleotide Synthesis, Gait, ed. (1984); Nucleic Acid Hybridization, Hames and Higgins, eds. (1984); and the series Methods in Enzymology, Colowick and Kaplan, eds, Academic Press, Inc., San Diego, Calif.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention.

As used herein the singular forms "a", "and", and "the" include plural reference unless the context clearly dictates otherwise. Thus, for example, reference to "a vector" is a reference to one or more vectors and includes equivalents thereof known to those skilled in the art.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent.

As used herein, the word "or" means any one member of a particular list and also includes any combination of members on that list.

The terms "comprises", "comprising", "includes", "including", "having" and their conjugates mean "including but not limited to". The term "consisting of means "including and limited to".

The term "consisting essentially of means that the composition, method or structure may include additional ingredients, steps and/or parts, but only if the additional ingredients, steps and/or parts do not materially alter the basic and novel characteristics of the claimed composition, method or structure.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals there between. As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), O-Beta Replicase systems, transcription-based amplification system (TAS) and strand displacement amplification (SDA). See, e.g., Diagnostic Molecular Microbiology: Principles and Applications, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) J. Gen. Microbiol. 139:425-32) can be modified to yield a functionally identical molecule. Accordingly, each silent variation of a nucleic acid, which encodes a polypeptide of the present invention, is implicit in each described polypeptide sequence and incorporated herein by reference.

A "control plant" or "control" as used herein may be a non-transgenic plant of the parental line used to generate a transgenic plant herein. A control plant may in some cases be a transgenic plant line that includes an empty vector or marker gene, but does not contain the recombinant polynucleotide of the present invention that is expressed in the transgenic plant being evaluated. A control plant in other cases is a transgenic plant expressing the gene with a constitutive promoter. In general, a control plant is a plant of the same line or variety as the transgenic plant being tested, lacking the specific trait-conferring, recombinant DNA that characterizes the transgenic plant. Such a progenitor plant that lacks that specific trait-conferring recombinant DNA can be a natural, wild-type plant, an elite, non-transgenic plant, or a transgenic plant without the specific trait-conferring, recombinant DNA that characterizes the transgenic plant. The progenitor plant lacking the specific, trait-conferring recombinant DNA can be a sibling of a transgenic plant having the specific, trait-conferring recombinant DNA. Such a progenitor sibling plant may include other recombinant DNA As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity or ligand/receptor binding is generally at least 30%, 40%, 50%, 60%, 70%, 80% or 90%, preferably 60-90% of the native protein for its native substrate. Conservative substitution tables providing functionally similar amino acids are well known in the art.

The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V) and
  6) Phenylalanine (F), Tyrosine (Y), Tryptophan (W).

See also, Creighton, Proteins, W.H. Freeman and Co. (1984).

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capricolumn* (Yamao, et al., (1985) Proc. Natl. Acad. Sci. USA 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "NUE nucleic acid" means a nucleic acid comprising a polynucleotide ("NUE polynucleotide") encoding a full length or partial length NUE polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) Guide To Molecular Cloning Techniques, from the series Methods in Enzymology, vol. 152, Academic Press, Inc., San Diego, Calif.; Sambrook, et al., (1989) Molecular Cloning: A Laboratory Manual, 2nd ed., vols. 1-3; and Current Protocols in Molecular Biology, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly plant is *Zea mays*.

One embodiment of the invention is use of the methods disclosed herein to predict a given phenotype (i.e. yield) for plants belonging to the plant family Poaceae. The Poaceae plant family comprises, as known in the art, many agronomically important grasses such as for example corn, wheat, rice, and sorghum.

Herein the term "growing season" or "growth cycle" interchangeably refers to a time period when a plant is undergoing active growth. As used herein, the phrase "one growing season" refers to the period from planting of a plant seed to the maturation of a plant and finally to the point where a plant is no longer undergoing active growth. The plant may cease active growth through natural processes (i.e. reaching the end of a growth cycle) or by other means such as harvest.

As used herein, "yield" may include reference to bushels per acre of a grain crop at harvest, as adjusted for grain moisture (15% typically for maize, for example), and the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated. Yield can be affected by many properties including without limitation, plant height, pod number, pod position on the plant, number of internodes, incidence of pod shatter, grain size, efficiency of nodulation and nitrogen fixation, efficiency of nutrient assimilation, carbon assimilation, plant architecture, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Yield of a plant of the can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are common practice in the art.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions.

Any suitable promoter sequence can be used by the nucleic acid construct of the present invention. According to some embodiments of the invention, the promoter is a constitutive promoter, a tissue-specific, or an abiotic stress-inducible promoter.

Suitable constitutive promoters include, for example, CaMV 35S promoter (SEQ ID NO:1546; Odell et al., Nature 313:810-812, 1985); *Arabidopsis* At6669 promoter (SEQ ID NO:1652; see PCT Publication No. WO04081173A2); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol. Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608, 144; 5,604,121; 5,569,597: 5,466,785; 5,399,680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al., Plant Mol Biol, 143). 323-32 1990), napA (Stalberg, et al., Planta 199: 515-519, 1996), Wheat SPA (Albanietal, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMBO3:1409-15, 1984), Barley ltr1 promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (PMB 32:1029-35, 1996)], embryo specific promoters [e.g., rice OSH1 (Sato et al., Proc. Natl. Acad. Sci. USA, 93: 8117-8122), KNOX (Postma-Haarsma of al, Plant Mol. Biol. 39:257-71, 1999), rice oleosin (Wu et al, J. Biochem., 123: 386, 1998)], and flower-specific promoters [e.g., AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3].

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267).

The term "Enzymatic activity" is meant to include demethylation, hydroxylation, epoxidation, N-oxidation, sulfooxidation, N-, S-, and O-dealkylations, desulfation, deamination, and reduction of azo, nitro, and N-oxide groups. The term "nucleic acid" refers to a deoxyribonucleotide or ribonucleotide polymer in either single- or double-stranded form, or sense or anti-sense, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof. The terms "operably linked", "in operable combination", and "in operable order" refer to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

A "structural gene" is that portion of a gene comprising a DNA segment encoding a protein, polypeptide or a portion thereof, and excluding the 5' sequence which drives the initiation of transcription. The structural gene may alternatively encode a nontranslatable product. The structural gene may be one which is normally found in the cell or one which is not normally found in the cell or cellular location wherein it is introduced, in which case it is termed a "heterologous gene". A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications that could affect biological activity or its characteristics, the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate splice junctions. The structural gene may be translatable or non-translatable, including in an anti-sense orientation. The structural gene may be a composite of segments derived from a plurality of sources and from a plurality of gene sequences (naturally occurring or synthetic, where synthetic refers to DNA that is chemically synthesized).

"Derived from" is used to mean taken, obtained, received, traced, replicated or descended from a source (chemical and/or biological). A derivative may be produced by chemical or biological manipulation (including, but not limited to, substitution, addition, insertion, deletion, extraction, isolation, mutation and replication) of the original source.

"Chemically synthesized", as related to a sequence of DNA, means that portions of the component nucleotides were assembled in vitro. Manual chemical synthesis of DNA may be accomplished using well established procedures (Caruthers, *Methodology of DNA and RNA Sequencing*, (1983), Weissman (ed.), Praeger Publishers, New York, Chapter 1); automated chemical synthesis can be performed using one of a number of commercially available machines.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, an "expression cassette" is a nucleic acid construct, generated recombinantly or synthetically, with a series of specified nucleic acid elements, which permit transcription of a particular nucleic acid in a target cell. The expression cassette can be incorporated into a plasmid, chromosome, mitochondrial DNA, plastid DNA, virus or nucleic acid fragment. Typically, the expression cassette portion of an expression vector includes, among other sequences, a nucleic acid to be transcribed and a promoter.

The terms "residue" or "amino acid residue" or "amino acid" are used interchangeably herein to refer to an amino acid that is incorporated into a protein, polypeptide or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.,* 138:267-84: $T_m$=81.5° C.+16.6 (log M)+0.41 (% GC)−0.61 (% form)—500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier, New York (1993); and *Current Protocols in Molecular Biology*, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C. and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

"Overexpression" refers to the level of expression in transgenic organisms that exceeds levels of expression in normal or untransformed organisms.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

"Preferred expression", "Preferential transcription" or "preferred transcription" interchangeably refers to the expression of gene products that are preferably expressed at a higher level in one or a few plant tissues (spatial limitation) and/or to one or a few plant developmental stages (temporal limitation) while in other tissues/developmental stages there is a relatively low level of expression.

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

A "selectable marker gene" refers to a gene whose expression in a plant cell gives the cell a selective advantage. The selective advantage possessed by the cells transformed with the selectable marker gene may be due to their ability to grow in presence of a negative selective agent, such as an antibiotic or a herbicide, compared to the ability to grow of non-transformed cells. The selective advantage possessed by the transformed cells may also be due to their enhanced capacity, relative to non-transformed cells, to utilize an added compound as a nutrient, growth factor or energy source. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

The term "transformation" refers to the transfer of a nucleic acid fragment into the genome of a host cell, resulting in genetically stable inheritance. "Transiently transformed" refers to cells in which transgenes and foreign DNA have been introduced (for example, by such methods as *Agrobacterium*-mediated transformation or biolistic bombardment), but not selected for stable maintenance. "Stably transformed" refers to cells that have been selected and regenerated on a selection media following transformation.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The term "translational enhancer sequence" refers to that DNA sequence portion of a gene between the promoter and coding sequence that is transcribed into RNA and is present in the fully processed mRNA upstream (5') of the translation start codon. The translational enhancer sequence may affect processing of the primary transcript to mRNA, mRNA stability or translation efficiency. "Visible marker" refers to a gene whose expression does not confer an advantage to a transformed cell but can be made detectable or visible. Examples of visible markers include but are not limited to Beta-glucuronidase (GUS), luciferase (LUC) and green fluorescent protein (GFP).

"Wild-type" refers to the normal gene, virus, or organism found in nature without any known mutation.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, and 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65 and Pearson, et al., (1994) *Meth. Mol. Biol.* 24:307-31. The preferred program to use for optimal global alignment of multiple sequences is PileUp (Feng and Doolittle, (1987) *J. Mol. Evol.,* 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40 and 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The phrase "abiotic stress" as used herein refers to any adverse effect on metabolism, growth, reproduction and/or viability of a plant by abiotic factors (i.e. water availability, heat, cold, and etc). Accordingly, abiotic stress can be induced by suboptimal environmental growth conditions such as, for example, salinity, water deprivation, water deficit, drought, flooding, freezing, low or high temperature (e.g., chilling or excessive heat), toxic chemical pollution, heavy metal toxicity, anaerobiosis, nutrient deficiency, nutrient excess, atmospheric pollution or UV irradiation.

The phrase "abiotic stress tolerance" as used herein refers to the ability of a plant to endure an abiotic stress without suffering a substantial alteration in metabolism, growth, productivity and/or viability.

As used herein "water deficit" means a period when water available to a plant is not replenished at the rate at which it is consumed by the plant. A long period of water deficit is colloquially called drought. Lack of rain or irrigation may not produce immediate water stress if there is an available reservoir of ground water for the growth rate of plants. Plants grown in soil with ample groundwater can survive days without rain or irrigation without adverse affects on yield. Plants grown in dry soil are likely to suffer adverse affects with minimal periods of water deficit. Severe water deficit stress can cause wilt and plant death; moderate drought can cause reduced yield, stunted growth or retarded development. Plants can recover from some periods of water deficit stress without significantly affecting yield. However, water deficit stress at the time of pollination can have an irreversible effect in lowering yield. Thus, a useful period in the life cycle of corn, for example, for observing water deficit stress tolerance is the late vegetative stage of growth before tasseling. Water deficit stress tolerance is determined by comparison to control plants. For instance, plants of this invention can survive water deficit stress with a higher yield than control plants. In the laboratory and in field trials drought can be simulated by giving plants of this invention and control plants less water than is given to sufficiently-watered control plants and measuring differences in traits. One aspect of the invention provides plants overexpressing the genes as disclosed herein which confers a higher tolerance to a water deficit.

As used herein, the phrase "water optimization" refers to any measure of a plant, its parts, or its structure that can be measured and/or quantified in order to assess an extent of or a rate of plant growth and development under different conditions of water availability. As such, a "water optimization trait" is any trait that can be shown to influence yield in a plant under different sets of growth conditions related to water availability. Exemplary measures of water optimization are grain yield at standard moisture percentage (YGSMN), grain moisture at harvest (GMSTP), grain weight per plot (GWTPN), and percent yield recovery (PYREC).

As used herein, the phrases "drought tolerance" and "drought tolerant" refer to a plant's ability to endure and/or thrive under conditions where water availability is suboptimal. In general, a plant is labeled as "drought tolerant" if it displays "enhanced drought tolerance." As used herein, the phrase "enhanced drought tolerance" refers to a measurable improvement, enhancement, or increase in one or more water optimization phenotypes as compared to one or more control plants.

Water Use Efficiency (WUE) is a parameter frequently used to estimate the tradeoff between water consumption and $CO_2$ uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of $CO_2$ uptake to water vapor loss from a leaf or portion of a leaf, often measured over a very short time period (e.g. seconds/minutes) (Kramer, 1983, p. 406). The ratio of $13C/12C$ fixed in plant tissue, and measured with an isotope ratio mass-spectrometer, also has been used to estimate WUE in plants using $C_3$ photosynthesis (Martin et al., 1999, Crop Sci. 1775). As used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients. It is contemplated that the transgenic plants produced by the methods described herein will confer an increase in water use efficiency.

The phrase "biotic stress" as used herein refers to any adverse effect on metabolism, growth, reproduction and/or viability of a plant by biotic factors (i.e. insect pressure, disease and etc).

The phrase "biotic stress tolerance" as used herein refers to the ability of a plant to endure an biotic stress without suffering a substantial alteration in metabolism, growth, reproduction and/or viability.

As used herein the phrase "plant biomass" refers to the amount (measured in grams of air-dry or dry tissue) of a tissue produced from the plant in a growing season, which could also determine or affect the plant yield or the yield per growing area.

As used herein the phrase "plant vigor" refers to the amount (measured by weight) of tissue produced by the plant in a given time. Hence increased vigor could determine or affect the plant yield or the yield per growing time or growing area.

The term "early vigor" refers to active healthy well-balanced growth especially during early stages of plant growth, and may result from increased plant fitness due to, for example, the plants being better adapted to their environment (optimizing the use of energy resources and partitioning between shoot and root). Plants having early vigor also show increased seedling survival and a better establishment of the crop, which often results in highly uniform fields (e.g. crops growing in a uniform fashion, such as the crops reaching various stages of development at substantially the same time), and often higher yields. Therefore, early vigor may be determined by measuring various factors, such as thousand kernel weight, percentage germination, percentage emergence, seedling growth, seedling height, root length, root and shoot biomass and many more.

As used herein, "seedling vigor" refers to the plant characteristic whereby the plant emerges from soil faster, has an increased germination rate (i.e., germinates faster), has faster and larger seedling growth and/or germinates faster under cold conditions as compared to the wild type or control under similar conditions. Seedling vigor has often been defined to comprise the seed properties that determine "the potential for rapid, uniform emergence and development of normal seedlings under a wide range of field conditions".

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase where the floral organs are produced. If the appropriate environmental and developmental signals the plant switches to floral, or reproductive, growth are disrupted, the plant will not be able to enter reproductive growth, therefore maintaining vegetative growth.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

As used herein, the term "allele" refers to any of one or more alternative forms of a gene, all of which relate to at least one trait or characteristic. In a diploid cell, two alleles of a given gene occupy corresponding loci on a pair of homologous chromosomes, although one of ordinary skill in the art understands that the alleles in any particular individual do not necessarily represent all of the alleles that are present in the species. Since the presently disclosed subject matter relates to SNPs, it is in some instances more accurate to refer to a "haplotype" (i.e., an allele of a chromosomal segment) instead of "allele". However, in such instances, the term "allele" should be understood to comprise the term "haplotype".

As used herein, the phrase "associated with" refers to a recognizable and/or assayable relationship between two entities. For example, a trait, locus, QTL, SNP, gene, marker, phenotype, etc. is "associated with resistance" if the presence or absence of the trait, locus, QTL, SNP, gene, marker, phenotype, etc., influences an extent or degree of tolerance.

As used herein, the term "backcross", and grammatical variants thereof, refers to a process in which a breeder crosses a progeny individual back to one of its parents, for example, a first generation hybrid F1 with one of the parental genotypes of the F1 hybrid. In some embodiments, a backcross is performed repeatedly, with a progeny individual of one backcross being itself backcrossed to the same parental genotype.

The term "chromosome" is used herein in its art-recognized meaning of the self-replicating genetic structure in the cellular nucleus containing the cellular DNA and bearing in its nucleotide sequence a linear array of genes.

As used herein, the terms "cultivar", "line" and "variety" refer to a group of similar plants that by structural or genetic features and/or performance can be distinguished from other varieties within the same species.

As used herein, the term "gene" refers to a hereditary unit including a sequence of DNA that occupies a specific location on a chromosome and that contains the genetic instruction for a particular characteristics or trait in an organism.

As used herein, the term "heterozygous" refers to a genetic condition existing when different alleles reside at corresponding loci on homologous chromosomes.

As used herein, the term "homozygous" refers to a genetic condition existing when identical alleles reside at corresponding loci on homologous chromosomes.

As used herein, the term "hybrid" in the context of nucleic acids refers to a double-stranded nucleic acid molecule, or duplex, formed by hydrogen bonding between complementary nucleotide bases. The terms "hybridize" or "anneal" refer to the process by which single strands of nucleic acid sequences form double-helical segments through hydrogen bonding between complementary bases.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous individual or line.

As used herein, the phrase "informative fragment" refers to a nucleic acid molecule and/or its nucleotide sequence that allows for the proper identification of which allele of an allele pair (e.g., an SNP) the nucleic acid molecule and/or the nucleotide sequence corresponds to.

As used herein, the terms "introgression", "introgressed", and "introgressing" refer to both a natural and artificial process whereby genomic regions of one species, variety, or cultivar are moved into the genome of another species, variety, or cultivar, by crossing those species. The process can optionally be completed by backcrossing to the recurrent parent.

As used herein, the term "linkage" refers to a phenomenon wherein alleles on the same chromosome tend to be transmitted together more often than expected by chance if their transmission was independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

In some embodiments, "linkage" implies physical proximity on a chromosome. Thus, two loci are linked if they are within 50 centiMorgans (cM) of each other. As such, two loci are linked if they are in some embodiments less than 10, in some embodiments 9, in some embodiments 8, in some embodiments 7, in some embodiments 6, in some embodiments 5, in some embodiments 4, in some embodiments 3, in some embodiments 2, and in some embodiments 1 centiMorgans (cM) of each other. For example, an SNP is linked to a marker if it is in some embodiments within 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "locus" refers to a position that a given gene or a regulatory sequence occupies on a chromosome of a given species. Thus, a "locus" is a chromosomal region where a polymorphic nucleic acid, trait determinant, gene or marker is located. For example, a "gene locus" is a specific chromosome location in the genome of a species where a specific gene can be found.

As used herein, the term "marker" refers to an identifiable position on a chromosome the inheritance of which can be monitored. In some embodiments, a marker comprises a known or detectable nucleic acid sequence.

A "metabolite marker" refers to any metabolite (e.g. glutamine, glucoside of glutamate, 5-oxoproline, aspartate, arginine, proline, phosphate, homoserine-lactone, leucine, putrescine, asparagine and the like) which can be measured in a plant part and correlated to predict a plant phenotype and/or trait. One aspect of the invention is the correlation of metabolite marker(s) to a plant's yield potential. Herein, "yield potential" or "future yield potential" interchangeably refers to the yield a plant will produce at a future time point following pollination (e.g. at harvest or seed at seed). One embodiment of the invention measures for metabolite marker(s) in a specific plant tissue prior to pollination such as un-pollinated female inflorescence tissue. The presence and/or absence of these metabolite markers can then be used to predict the approximate yield of a given plant post-pollination (e.g. at seed maturity, or harvest). The metabolite may have a negative or positive correlation with a yield phenotype and still be predictive of yield.

As used herein, the phrase "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion and deletion mutations (INDEL), microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

As used herein, the term "offspring" plant refers to any plant resulting as progeny from a vegetative or sexual reproduction from one or more parent plants or descendants thereof. For instance an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings of F1s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

As used herein, the term "phenotype" refers to a detectable characteristic of a cell or organism, which characteristics are at least partially a manifestation of gene expression.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like. Herein the term "un-pollinated female inflorescence tissue" refers to any un-pollinated female reproductive tissue of a plant (e.g. spiklet, bracht, spikelet meristem, inflorescence stalk tissue, immature floral tissue, and immature ear shoots). The term also refers to all associated and/or adjacent tissues that attach to said un-pollinated female inflorescence tissue.

As used herein, the term "population" refers to a genetically heterogeneous collection of plants sharing a common genetic derivation.

As used herein, the term "primer" refers to an oligonucleotide which is capable of annealing to a nucleic acid target allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH).

As used herein, the term "regenerate", and grammatical variants thereof, refers to the production of a plant from tissue culture.

As used herein, the term "tolerant" and "tolerance" encompass both partial and full tolerance to herbicide injury (e.g., phytotoxicity caused by a HPPD inhibiting herbicide). For HPPD inhibiting herbicides, "phytoxicity" occurs in a range from minor chlorosis (discoloration) to necrosis. A susceptible plant can either be non-tolerant or have lower levels of tolerance to herbicide damage relative to a tolerant plant. The term is used to include such separately identifiable forms of resistance as "full resistance", "immunity", "intermediate resistance", "partial resistance", and "hypersensitivity".

DETAILED DESCRIPTION OF THE INVENTION

The embodiments herein provide methods and compositions related to predicting plant yield utilizing an unexpected correlation of specific plant metabolite levels alone or in combination in sampled un-pollinated plant reproductive tissue. In one embodiment the sampled un-pollinated plant reproductive tissue is un-pollinated female inflorescence tissue. In some embodiments the tissue may be sampled from the stalk of the un-pollinated inflorescence tissue.

Plant metabolites taken from un-pollinated plant reproductive tissue and/or adjacent tissue that may be correlated with predicted plant yield, herein referred to as "s" may include but are not limited to amino acids, nutrients (e.g. phosphate, calcium, nitrogen, etc), organic acids, organic bases, sugars (simple or complex), proteins, nucleic acids or molecules containing fatty acid chains. In one embodiment the yield metabolite markers comprise either individually or any combination of glutamine, glucoside of glutamate, 5-oxoproline, aspartate, arginine, proline, phosphate, homoserine-lactone, leucine, asparagines, putrescine, valine, vanillate, threonine, adenine, aminpentanoate, erythritol, nicotinate ribonucleoside, arginine, 1,3-dihydroxyacetone, isoleucylglutamate, lysine, methyl-2-oxopentanoate, 3-methoxytyrosine, N6-acetyllysine, 2-aminoadipate, and the like. In one embodiment, the yield metabolite markers are selected from one or more of glutamine, glucoside of glutamate, 5-oxoproline, aspartate, arginine, proline, phosphate, homoserine-lactone, leucine, asparagines, and putrescine. In another embodiment, the yield metabolite markers comprise glutamine, valine and vanillate. In another embodiment, the yield metabolite markers include homoserine lactone, threonine, adenine, aminpentanoate, erythritol, nicotinate ribonucleoside, arginine, 1,3-dihydroxyacetone, isoleucylglutamate, lysine, and methyl-2-oxopentanoate. In another embodiment, the yield metabolite markers include markers that are positively correlated with yield, such as, but not limited to, glutamine, glucoside of glutamate, 5-oxoproline, aspartate, arginine, proline, phosphate, homoserine-lactone, leucine, asparagines, and putrescine. Alternatively, the yield metabolite markers could include one or more markers that are negatively correlated with yield, such as, but not limited to, 3-methoxytyrosine, N6-acetyllysine and 2-aminoadipate. In another embodiment, the yield metabolite marker is glutamine.

The embodiments disclosed herein may be used to predict yield in any monocot or dicot plant for example but not limited to maize, soybean, barley, alfalfa, sunflower, canola, soybean, cotton, peanut, sorghum, tobacco, sugar beet, rice, wheat, rye, turfgrass, millet, sugarcane, tomato, or potato. In one embodiment the invention may be used to predict yield in a monocot plant or plant population. A further embodiment is the invention may be used to predict yield (i.e. grain yield) in a plant selected from the Poaceae or "true grass" family (e.g. maize, rice, wheat and sorghum). The methods described herein may also be employed in predicting yield in either transgenic or non-transgenic plants.

Some aspects of the invention may relate to the prediction of grain yield in a plant wherein the grain yield may be predicted in a unit per plant. For example one may be enabled by the teachings described herein to predict the amount of biomass weight per plant or grain weight per plant. In some embodiments one may calculate the approximate number of kernels produced per plant. In some aspects one may be able to predict the amount of a plant product that may be produced from a plant and or plant population for instance, the amount of ethanol predicted to be produced from a relative plant yield prediction.

It is contemplated in that one may use common statistical methods to sample a subset of plants from a homogenous population of plants and use the methods described herein to predict the approximate combined yield of said homogenous population of plants. This method would be highly valuable in commercial agriculture in that one could for example predict the amount of grain a given crop population will yield. Using these predictions, a grower could anticipate whether or not more fertilizer should be applied to the field. In some instances, one could use these methods to anticipate irrigation water usage.

In one aspect of the invention, the yield metabolite markers are measured in any one of or in combination with spikelet tissue, bract tissue spikelet meristem tissue, inflorescence stalk tissue or immature floral tissue from a monocot plant.

Immature floral tissue can include immature ear shoots. In one embodiment the monocot plant is a member of the Poaceae family. In another aspect of the invention immature ear shoots of maize are sampled for yield metabolite markers whose levels can then be correlated to the plant's predicted yield.

Metabolite profiling was performed to identify small molecules that may be useful in predicting yield in plants. In some aspects these metabolites are measured in specific tissues (e.g. unpollinated female reproductive tissue) or may be measured in any tissue or multiple plant tissues. There are various methods for measuring metabolites including, for example, HPLC (high-performance liquid chromatography), spectrophotometry, enzymatic determination or chemical analysis. Techniques for metabolite profiling are well known in the art. See e.g., U.S. Pat. Nos. 7,005,255; 7,329,489; 7,433,787; 7,550,258; 7,550,260; and 7,553,616 and U.S. Published Application Nos. 20020009740; 20040146853; 20050014132; 20060134676, 20060134677; 20060134678; 20070172820; 20070172885; 20010178599; 20070026389; 20070032969; 20070288174; 20070298998; 20080124752; 20080161228; 20090017464; 20090075284; 20090093971; and 20090155826 all incorporated by reference. Biomarkers of yield identified herein include molecules associated with for example nitrogen use, stress responses, or sugar pathways.

The use of metabolite profiling data allows for the identification of nucleic acids useful in possibly increasing yield in plants which include nucleic acids encoding components of the nitrogen assimilation pathway in plants. In one aspect it may be beneficial to express an protein involved in the nitrogen assimilation pathway specifically in the un-pollinated female reproductive tissue of a plant. Previously described nucleic acids and proteins have not taught how to use such molecules for enhancing drought tolerance in plants.

Specifically, when performing methods as described herein, nucleic acids useful in the invention include (a) full length or functional fragments encoding glutamine synthetase, glutamate dehydrogenase, aspartate aminotransferase, and asparagine synthetase, which may be overexpressed in a plant to thereby confer drought tolerance to the plant and/or for identification of activators of such enzymes; (b) full length or functional fragments encoding allantoinase, allantoate amidohydrolase, and ureidoglycolate amidohydrolase, which may be used for identification of inhibitors of such enzymes; and (c) inhibitory nucleic acids having homology to a nucleic acid encoding allantoinase, allantoate amidohydrolase, and ureidoglycolate amidohydrolase, which may be expressed in a plant to thereby confer drought tolerance to the plant.

The following enzymes and associated referenced accession number and sequences may find use in many in various embodiments as described herein:

Glutamine synthetase (GS, EC 6.3.1.2) catalyzes the ATP-dependent synthesis of glutamine via the condensation of ammonium and glutamate to yield glutamine, which then provides nitrogen groups, either directly or via glutamate, for the biosynthesis of all nitrogenous compounds in the plant. Higher plants have two types of GS isoenzymes that are localized in the cytosol or in the plastid/chloroplasts. Representative nucleic acids encoding cytosolic GS isoenzymes include maize GS1-1, GS1-2, GS1-3, GS1-4, and GS1-5 (GenBank Accession Nos. X65926, X65927, X65928, X65929, and NM_001111827 respectively). A representative nucleic acid encoding a plastid GS isoenzyme is maize GS-2 (GenBank Accession No. X65931). A representative nucleic acid encoding a cytosolic GS isoenzyme from pea (GenBank Accession No. PEAGSCY1A).

Glutamate dehydrogenase (GDH, EC 1.4.1.3) catalyzes the synthesis of glutamate via the condensation of ammonium and alpha ketoglutarate. A representative nucleic acid encoding glutamate dehydrogenase is maize glutamate dehydrogenase (GenBank Accession Nos. gdh1:NM_001111831.1).

Aspartate aminotransferase (AspAT, EC 2.6.1.1) catalyzes the conversion of oxaloacetate to aspartate. A representative nucleic acid encoding aspartate aminotransferase is maize aspartate aminotransferase (GenBank Accession Nos. NM_001155533.1).

Asparagine synthetase (EC 6.3.5.4) catalyzes three distinct chemical reactions: glutamine hydrolysis to yield ammonia takes place in the N-terminal domain. The C-terminal active site mediates both the synthesis of a beta-aspartyl-AMP intermediate and its subsequent reaction with ammonia. The ammonia released is channeled to the other active site to yield asparagine. Representative nucleic acids encoding asparagine synthetase include maize asparagine synthetase 1, asparagine synthetase 2, and asparagine synthetase 3 (GenBank NM_001111997, NP_001131013, AsnS2: NM_001137541, NP_001131014, AsnS3:NM_001137542, NP_001131015, and AsnS4:NM_001137543), respectively. Representative nucleic acids encoding asparagine synthetase 1 from *Glycine max* (GenBank Accession No. U77679.1).

Allantoinase (EC 3.5.2.5) catalyzes the conversion of allantoin to allantoate. Representative nucleic acids encoding allantoinase include maize allantoinase (GenBank Accession No. NM_001148584, EU973141, NP_001142056) respectively. Rice allantoinase (GenBank Accession No. NM_001060821). *Arabidopsis thaliana* allantoinase (GenBank Accession No. NP_567276). A *Robinia pseudocacia* allantoinase nucleic acid (GenBank Accession No. AY466437). A *Saccharomyces cerevisiae* allantoinase nucleic acid (GenBank Accession No. YSCDAL1A).

Allantoate Amidohydrolase (EC 3.5.3.9, allantoate deiminase) catalyzes the conversion of allantoate to ureidoglycine. Representative nucleic acids encoding allantoate amidohydrolase include maize allantoate amidohydrolase (GenBank Accession No. NM_001157773), soybean allantoate amidohydrolase (GenBank Accession No. FJ796239), and *Arabidopsis thaliana* allantoate amidohydrolase (GenBank Accession Nos. NM_118126 and NP_193740.1), respectively.

Ureidoglycolate Amidohydrolase (EC 3.5.3.19) catalyzes the conversion of ureidoglycolate to glycoxylate. Representative nucleic acids encoding ureidoglycolate amidohydrolase include *Arabidopsis thaliana* ureidoglycolate amidohydrolase (GenBank Accession No. NM_123726.3 and NC_003076) and Baker's yeast ureidoglycolate amidohydrolase (GenBank Accession No. UAH: NP_012298, respectively).

Nucleic acid variants of the above-identified sequences, which are useful in the methods of the present invention, are described herein below.

Nucleic acids are deoxyribonucleotides or ribonucleotides and polymers thereof in single-stranded, double-stranded, or triplexed form. Unless specifically limited, the term encompasses nucleic acids containing known analogues of natural nucleotides that have similar properties as the reference natural nucleic acid. The terms nucleic acid molecule or nucleic acid may also be used in place of gene, cDNA, mRNA, or cRNA. Nucleic acids may be synthesized, or may be derived from any biological source, including any organism.

Substantially identical nucleic acids are also identified as nucleic acids that hybridize specifically to or hybridize substantially to the full length of any one of sequences disclosed herein under stringent conditions. In the context of nucleic acid hybridization, two nucleic acid sequences being compared may be designated a probe and a target. A probe is a reference nucleic acid molecule, and a target is a test nucleic acid molecule, often found within a heterogeneous population of nucleic acid molecules. A target sequence is synonymous with a test sequence.

A particular nucleotide sequence employed for hybridization studies or assays includes probe sequences that are complementary to at least an about 14 to 40 nucleotide sequence of a nucleic acid molecule of the present invention. For example, probes may comprise 14 to 20 nucleotides, or even longer where desired, such as 30, 40, 50, 60, 100, 200, 300, or 500 nucleotides or up to the full length of any one sequence as referenced herein. Such fragments may be readily prepared, for example by chemical synthesis of the fragment, by application of nucleic acid amplification technology, or by introducing selected sequences into vectors for recombinant production.

Specific hybridization refers to the binding, duplexing, or hybridizing of a molecule only to a particular nucleotide sequence under stringent conditions when that sequence is present in a complex nucleic acid mixture (e.g., total cellular DNA or RNA). Specific hybridization may accommodate mismatches between the probe and the target sequence depending on the stringency of the hybridization conditions.

Stringent hybridization conditions and stringent hybridization wash conditions in the context of nucleic acid hybridization experiments such as Southern and Northern blot analysis are both sequence-dependent and environment-dependent. Longer sequences hybridize specifically at higher temperatures. An extensive guide to the hybridization of nucleic acids is found in Tijssen, *Laboratory Techniques in Biochemistry and Molecular Biology-Hybridization with Nucleic Acid Probes*, 1993, part I chapter 2, Elsevier, New York, N.Y. Generally, highly stringent hybridization and wash conditions are selected to be about 5° C. lower than the thermal melting point (Tm) for the specific sequence at a defined ionic strength and pH. Typically, under stringent conditions a probe will hybridize specifically to its target subsequence, but to no other sequences.

The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook et al., eds., *Molecular Cloning: A Laboratory Manual*, 1989, Cold Spring Harbor Laboratory Press, Cold Spring Harbor, N.Y., for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1M Na+ ion, typically about 0.01 to 1M Na+ ion concentration (or other salts) at pH 7.0-8.3, and the temperature is typically at least about 30° C. Stringent conditions may also be achieved with the addition of destabilizing agents such as formamide. In general, a signal to noise ratio of 2-fold (or higher) than that observed for an unrelated probe in the particular hybridization assay indicates detection of specific hybridization.

The following are examples of hybridization and wash conditions that may be used to identify nucleotide sequences that are substantially identical to reference nucleotide sequences of the present invention: a probe nucleotide sequence hybridizes to a target nucleotide sequence in 7% sodium dodecyl sulphate (SDS), 0.5M NaPO$_4$, 1 mM EDTA at 50° C. followed by washing in 2×SSC, 0.1% SDS at 50° C.; such as, a probe and target sequence hybridize in 7% sodium dodecyl sulphate (SDS), 0.5M NaPO$_4$, 1 mM EDTA at 50° C. followed by washing in 1×SSC, 0.1% SDS at 50° C.; such as, a probe and target sequence hybridize in 7% sodium dodecyl sulphate (SDS), 0.5M NaPO4, 1 mM EDTA at 50° C. followed by washing in 0.5×SSC, 0.1% SDS at 50° C.; such as, a probe and target sequence hybridize in 7% sodium dodecyl sulphate (SDS), 0.5M NaPO4, 1 mM EDTA at 50° C. followed by washing in 0.1×SSC, 0.1% SDS at 50° C.; such as, a probe and target sequence hybridize in 7% sodium dodecyl sulphate (SDS), 0.5M NaPO4, 1 mM EDTA at 50° C. followed by washing in 0.1×SSC, 0.1% SDS at 65° C.; or such as, a probe and target sequence hybridize in a solution of 6×SSC (0.5% SDS) at 65° C. followed by washing in 2×SSC (0.1% SDS) and 1×SSC (0.1% SDS).

A further indication that two nucleic acid sequences are substantially identical is that proteins encoded by the nucleic acids are identical or substantially identical, share an overall three-dimensional structure, or are biologically functional equivalents, as described further herein below. Nucleic acid molecules that do not hybridize to each other under stringent conditions are still substantially identical if the corresponding proteins are substantially identical. This may occur, for example, when two nucleotide sequences encoding a same protein sequence differ as permitted by the genetic code, i.e., nucleotide sequences having degenerate codon substitutions wherein the third position of one or more selected (or all) codons is substituted with mixed-base and/or deoxyinosine residues. See Batzer et al., *Nucleic Acids Res.*, 1991, 19:5081; Ohtsuka et al., *J. Biol. Chem.*, 1985, 260:2605-2608; and Rossolini et al. *Mol. Cell Probes*, 1994, 8:91-98.

Nucleic acids useful in the invention also can comprise a mutagenized nucleotide sequence, including sequences comprising silent mutations. A mutation may comprise one or more residue changes, a deletion of one or more residues, or an insertion of one or more additional residues.

For example, nucleic acids useful in the invention also comprise nucleic acids of any one of the sequences referenced herein, which have been altered for expression in the host organism to account for differences in codon usage. For example, the specific codon usage in plants differs from the specific codon usage in certain microorganisms. Comparison of the usage of codons within a cloned microbial open reading frame to usage in plant genes (and in particular genes from the target plant) will enable an identification of the codons within the open reading frame that should specifically be changed. Typically plant evolution has tended towards a strong preference of the nucleotides C and G in the third base position of monocotyledons, whereas dicotyledons often use the nucleotides A or T at this position. Plant genes typically have a GC content of more than 35%. Open reading frame sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites. By modifying a gene to incorporate specific codon usage for a particular target transgenic species, problems associated with GC/AT content and illegitimate splicing will be overcome.

Nucleic acids useful in the invention also include nucleic acids complementary to any sequence referenced herein or variants thereof as described herein. Complementary sequences are two nucleotide sequences that comprise antiparallel nucleotide sequences capable of pairing with one another upon formation of hydrogen bonds between base pairs. As used herein, the term complementary sequences means nucleotide sequences which are substantially complementary, as may be assessed by the same nucleotide comparison methods set forth below, or is defined as being capable of hybridizing to the nucleic acid segment in question under relatively stringent conditions such as those described herein. A particular example of a complementary nucleic acid segment is an antisense oligonucleotide.

When preparing any of the foregoing nucleic acid variants encoding a functional glutamine synthetase, glutamate dehydrogenase, aspartate aminotransferase, or asparagine synthetase enzyme, it is expected that conservative amino acid changes introduced in identifiable functional domains of such enzymes would not result in a change of enzymatic activity. Such identifiable functional domains are summarized below with respect to representative sequences. By performing routine alignments between the disclosed representative sequences and variant sequences described herein, one skilled in the art could readily identify corresponding functional domains in the variant sequences as well. Likewise, it is expected that conservative or non-conservative amino acid substitutions introduced outside of such domains would also not result in a change of enzymatic activity.

A conservatively substituted variant refers to a polypeptide comprising an amino acid sequence in which one or more residues have been conservatively substituted with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Glutamine synthetase possess a beta Grasp domain having the consensus sequence [FYWL]-D-G-S-S-x(6,8)-[DEN-QSTAK]-[SA]-[DE]-x(2)-[LIVMFY](SEQ ID NOS: 1-3), and ATP binding domain, and a catalytic glutamate-ammonia ligase activity domain. The locations of the beta-Grasp domain and catalytic domains are exemplified by GS1-5, GS1-1, and GS2. For example, GS1-5 has a beta-Grasp domain (this binding site is referred to on PFAM as pfam03951) that includes amino acids 17-97 and a catalytic domain that includes amino acids 103-354 (pfam00120). GS1-1 has a beta-Grasp domain (pfam03951) that includes amino acids 68-148 and a catalytic domain that includes amino acids 154-405. GS2 has a beta-Grasp domain (pfam03951) that includes amino acids 17-97 and a catalytic domain that includes amino acids 103-353. The crystal structure of GS has been described, which can also be used to identify residues that may be changed while preserving the enzyme structure and function. See Unno et al., *J. Biol. Chem.*, 2006, 281(39):29287-29296.

Glutamate dehydrogenase contains an ELFV_dehydrogen_N domain that includes amino acids 31-161; a NADP binding domain that includes amino acids 176-402; and a NADP binding site that includes amino acids 215-217, 237-238, 289-290, and 310-312. NAD binding involves numerous hydrogen-bonds and van der Waals contacts, in particular H-bonding of residues in a turn between the first strand and the subsequent helix of the Rossmann-fold topology. Characteristically, this turn exhibits a consensus binding pattern similar to GXGXXG (SEQ ID NO: 4), in which the first 2 glycines participate in NAD(P)-binding, and the third facilitates close packing of the helix to the beta-strand. Glutamate dehydrogenase may contain a second domain in addition to the NADP domain, which is responsible for specifically binding a substrate and catalyzing a particular enzymatic reaction.

Aspartate aminotransferase is a pyridoxal phosphate (PLP)-dependent enzyme of fold type I having a pyridoxal 5'-phosphate (PLP) binding site that includes amino acids 159-161, 187, 240, 271, 301, 303-304, and 312; an AAT_like region that includes amino acids 86-451; a homodimer interface that includes amino acids 162, 197, 264, 310-312, 348, and 351; and a catalytic residue that includes amino acid 304.

Asparagine synthetase 1 from corn has an active site that includes amino acids 2, 50, 75-77, and 98; a dimer interface site that includes amino acids 17, 25, 28, 32-36, 49; a ligand binding site that includes amino acids 231-233, 265-267, 327, 341-343; and a molecular tunnel that includes amino acids 231-233, 265-267, 327, 341-343.

Asparagine synthetase 2 has an active site that includes amino acids 2, 52, 77-79, an 102; a dimer interface site that includes amino acids 20, 28, 31, 34-38, and 51; a ligand binding site that includes amino acids 248-250, 282-284, 344, and 358-360; and a molecular tunnel that includes amino acids 248-250, 282-284, 344, and 358-360.

Asparagine synthetase 3 has an active site that includes amino acids 2, 50, 75-77 and 99; a dimer interface site that includes amino acids 18, 26, 29, 32-36, and 49; a ligand binding site that includes amino acids 232-234, 266-268, 328, 342-344; and a molecular tunnel that includes amino acids 232-234, 266-268, 328, and 342-344.

Asparagine synthetase 4 has an active site that includes amino acids 2, 50, 75-77, and 99; a dimer interface site that includes amino acids 18, 26, 29, 32-36, and 49; a ligand binding site that includes amino acids 232-234, 266-268, 328, and 342-344; and a molecular tunnel that includes amino acids 232-234, 266-268, 328, and 342-344.

Nucleic acids as described herein may be cloned, synthesized, altered, mutagenized, or combinations thereof. Standard recombinant DNA and molecular cloning techniques used to isolate nucleic acids are known in the art. Site-specific mutagenesis to create base pair changes, deletions, or small insertions is also known in the art. See e.g., Sambrook et al. (eds.) *Molecular Cloning: A Laboratory Manual*, 1989, Cold Spring Harbor Laboratory Press, Cold Spring Harbor, N.Y.; Silhavy et al., *Experiments with Gene Fusions*, 1984, Cold Spring Harbor Laboratory Press, Cold Spring Harbor, N.Y.; Glover & Hames, *DNA Cloning: A Practical Approach*, 2nd ed., 1995, IRL Press at Oxford University Press, Oxford/New York; Ausubel (ed.) *Short Protocols in Molecular Biology*, 3rd ed., 1995, Wiley, New York.

The present invention also provides inhibitory nucleic acids having homology to nucleic acids encoding allantoinase, allantoate amidohydrolase, and ureidoglycolate amidohydrolase, which are the targets for inhibition Inhibitory nucleic acids are well-known in the art, including nucleic acids for cosuppression, antisense inhibition, viral-suppression, hairpin suppression, stem-loop suppression, double-stranded RNA-inhibition, and interfering RNAs (e.g., short interfering RNAs (siRNA) and microinterfereing RNAs (miRNA)).

Antisense inhibition refers to the production of antisense RNA transcripts capable of suppressing the expression of the target gene or gene product. Antisense RNA refers to an RNA transcript that is complementary to all or part of a target primary transcript or mRNA and that blocks the expression of a target isolated nucleic acid fragment (U.S. Pat. No. 5,107,065). The complementarities of an antisense RNA may be with any part of the specific gene transcript, i.e., at the 5' non-coding sequence, 3' non-coding sequence, introns, or the coding sequence.

Cosuppression refers to the production of sense RNA transcripts capable of suppressing the expression of the target gene or gene product. Sense RNA is an RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence. See e.g., Vaucheret et al., *Plant J.*, 1998, 16:651-659 and Gura, *Nature*, 2000, 404:804-808.

Another variation describes the use of plant viral sequences to direct the suppression of proximal mRNA encoding sequences. See e.g., PCT International Publication No. WO 98/36083.

Inhibitory nucleic acids may comprise hairpin structures that incorporate all, or part, of an mRNA encoding sequence in a complementary orientation that results in a potential stem-loop structure for the expressed RNA. See e.g., PCT International Publication No. WO 99/53050. In this case, the stem is formed by polynucleotides having homology to the target sequence inserted in either sense or anti-sense orientation with respect to the promoter, and the loop is formed by polynucleotides that do not have a complement in the construct. Hairpin structures may increase the frequency of cosuppression or silencing in the recovered transgenic plants. For a review of hairpin suppression, see Wesley et al., *Methods in Molecular Biology, Plant Functional Genomics: Methods and Protocols,* 2003, 236:273-286 and PCT International Publication Nos. WO 99/61632, WO 02/00894, WO 02/00904.

RNA interference refers to the process of sequence-specific post-transcriptional gene silencing in animals mediated by short interfering RNAs (siRNAs). See e.g., Fire et al., *Nature,* 1998, 391:806. The corresponding process in plants is commonly referred to as post-transcriptional gene silencing (PTGS) or RNA silencing. The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., *Nature,* 2001, 409:363). Short interfering RNAs derived from dicer activity are typically about 21 to about 23 nucleotides in length and comprise about 19 base pair duplexes (Elbashir et al., *Genes Dev.,* 2001, 15:188). Dicer has also been implicated in the excision of 21- and 22-nucleotide small temporal RNAs (stRNAs) from precursor RNA of conserved structure that are implicated in translational control (Hutvagner et al., *Science,* 2001, 293:834 (2001)). The RNAi response also features an endonuclease complex, commonly referred to as an RNA-induced silencing complex (RISC), which mediates cleavage of single-stranded RNA having sequence complementarities to the antisense strand of the siRNA duplex. Cleavage of the target RNA takes place in the middle of the region complementary to the antisense strand of the siRNA duplex. In addition, RNA interference can also involve small RNA (e.g., miRNA) mediated gene silencing, presumably through cellular mechanisms that regulate chromatin structure and thereby prevent transcription of target gene sequences. See, e.g., Allshire, *Science,* 2002, 297:1818-1819; Volpe et al., *Science,* 2002, 297:1833-1837; Jenuwein, *Science,* 2002, 297:2215-2218; and Hall et al., *Science,* 2002, 297:2232-2237.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

Sequence complementarities between small RNAs and their RNA targets may determine which mechanism, RNA cleavage or translational inhibition, is employed. While not intending to be limited by a particular mode of action, perfect or near-perfect complementary siRNAs are thought to mediate RNA cleavage, whereas miRNA/target duplexes containing many mismatches may mediate translational inhibition.

MicroRNAs (miRNAs) are noncoding RNAs of about 19 to about 24 nucleotides, which are processed from longer precursor transcripts that range in size from approximately 70 to 200 nt. See e.g., Lagos-Quintana et al., *Science,* 2001, 294:853-858, Lagos-Quintana et al., *Curr. Biol.,* 2002, 12:735-739; Lau et al., *Science,* 2001, 294:858-862; Lee et al., *Science,* 2001, 294:862-864; Llave et al., *Plant Cell,* 2002, 14:1605-1619 (2002); Mourelatos et al., *Genes Dev.,* 2002, 16:720-728; Park et al., *Curr. Biol.,* 2002, 12:1484-1495; Reinhart et al., *Genes Dev.,* 2002, 16:1616-1626. Processing of miRNA precursors is mediated by DCL1 (previously named CARPEL FACTORY/SHORT INTEGUMENTS1/SUSPENSOR1). See e.g., Park et al., *Curr. Biol.,* 2002, 12:1484-1495; Reinhart et al., *Genes Dev.,* 2002, 16:1616-1626. MicroRNAs (miRNAs) appear to regulate target genes by binding to complementary sequences located in the transcripts produced by these genes. Binding of miRNA may cause downregulation of steady-state levels of the protein encoded by the target mRNA without affecting the transcript itself (see e.g., Olsen and Ambros, *Dev. Biol.,* 1999, 216:671-610) or may cause specific RNA cleavage of the target transcript within the target site (see e.g., Hutvagner et al., Science, 2002, 297:2056-2060; Llave et al., *Plant Cell,* 2002, 14:1605-1619). Accordingly, it appears that miRNAs can enter at least two pathways of target gene regulation: (1) protein downregulation when target complementarities is <100%; and (2) RNA cleavage when target complementarities is 100%. MicroRNAs entering the RNA cleavage pathway are analogous to the 21-25 nucleotide short interfering RNAs (siRNAs) generated during posttranscriptional gene silencing (PTGS). Inhibitory nucleic acid molecules as described herein above can be used to mediate gene silencing via interaction with RNA transcripts or alternately by interaction with particular gene sequences, wherein such interaction results in gene silencing either at the transcriptional or post-transcriptional level. Inhibitory nucleic acids useful in the invention may have perfect or near-perfect complementarities with a target allantoinase, allantoate amidohydrolase, and ureidoglycolate amidohydrolase molecule, or may have several mismatches.

One aspect of the invention, is the use of yield metabolite markers as a method to select for high yielding plant lines. For example, one may measure yield metabolite markers in immature ear shoots of a maize plant and predict yield for a given plant. These high yielding plants could then be used to introgress with hybrid lines and further screened for higher yielding crosses by traditional validation methods of measuring yield from mature plant and/or measuring yield metabolite markers and correlating predicted yield as described herein. The ability to predict yield in a plant also would be a valuable tool in evaluating transgenic and/or non-transgenic traits for yield. Having such a predictive tool would enable one to more quickly evaluate traits for yield as well as reduce costs compared to current practices in that plants would not have to be grown to maturity. Additionally, one may be able to evaluate less plants as to whether or not a given trait would have higher yields relative to controls.

In one aspect of the invention, the methods described herein may be useful in farm management and business methods. For instance, the ability to predict yield in a plant population would enable better crop forecasting abilities than the current methods employed. It is contemplated that sub-sampling of large populations of crops using well known statistical methods and predicting the relative yield of this population would allow for better management of crop harvesting, seed collection and handling and transportation associated with moving harvested materials. For instance, a grower could thus predict how much grain they would obtain from a given population of crops using the methods as described herein. By predicting the amount of grain, a grower can then better plan for and manage such aspects as harvest of the crop, handling and storage of the grain, transportation of the grain and possible income that will be generated from the crop. It is contemplated that the yield prediction methods taught herein may also be highly valuable for organizations such as ethanol plants in that one could predict the amount of ethanol that can be produced from a given population of crops via using the yield prediction methods taught herein for that population of crops. It is also envisioned that the predictive methods disclosed herein, could also be very valuable in predicting associated costs of a given crop such as for example chemical applications, fertilizer or irrigation applications.

Another aspect of the invention is that the methods as described herein may be useful in providing a means to calculate and/or managing risk associated with growing and harvesting crops. For instance, the methods described herein could be useful in evaluating risk(s) of a particular crop. A coefficient representive of this risk then may be used in calculating for example crop insurance rates for a given crop. It is contemplated that if a particular crop is expected to result in a high yield as indicated by the methods described herein, one could receive a discounted rate of insurance. For instance the yield predictive methods as described herein could be used in conjunction with any one or more of the business methods as described in U.S. Pat. Nos. 7,657,469, 7,039,592, U.S. 20090112637, U.S. U.S. 20080086340, U.S. Pat. No. 7,356, 406, U.S. 20080040165, U.S. 20060287896, U.S. 20060282294, U.S. 2006001523, U.S. 20060015360, U.S. 20060015374, U.S. 20050125260, U.S. 20050027572, U.S. 20030061075 and U.S. 20020173980 herein all incorporated by reference.

A crop may include, any type of edible or inedible agricultural product, grain, oilseed, fiber, fruit, nut, seed, or vegetable or any other material produced by a genetically modified plant or non-genetically modified plant. A defined attribute may comprise one or more of the following characteristics of any crop: organic, organically grown, high oil, high protein, high starch, waxy, highly fermentable, color, grade, classification, weight, nutritionally enhanced, pest resistant, herbicide resistant, pesticide resistant, fungicide resistant, drought tolerant, freeze tolerant, mildew resistant, bacterial resistant, disease resistant, non-genetically modified, genetically modified, genetically altered protein content, genetically altered enzyme content, genetically altered sugar content, genetically altered starch content, high protein, yield enhanced, pharmaceutical traits, precursors or ingredients, pharmaceutical properties, medicinal properties, genetically resistant to cross-pollination (e.g., a teosinte gene cluster introduced into corn deoxyribonucleic (DNA) acid) from neighboring genetically modified crops, and any other crop attributes.

A defined attribute may represent any plant trait associated with a crop, an agricultural product derived from the crop, or both. Further, the defined attribute may comprise a characteristic that is associated with a particular level or range of levels of any of the following: a plant trait, protein, oil, starch in plant material (e.g., harvested grain, fiber or oilseed). For example, soy meal having a certain characteristic (e.g., a minimum percent protein content by volume or weight) may be derived from soybeans as the crop. The defined attribute may be, but need not be, defined with respect to a corresponding attribute of a commodity crop, an agricultural product derived from a commodity crop, or another reference.

Although any generally accepted grading standard (e.g., a standard adopted by the Chicago Board of Trade or elsewhere within the marketplace) may be used to define a commodity crop, the generally accepted grading standards may not address a defined attribute or another particular characteristic of interest (e.g., corn with a predicted yield output). Accordingly, the defined attributes may be defined in accordance with one or more of the following items: (1) reference genetic profile (e.g., for pharmaceutical crops or other genetically modified crops), (2) identity of a gene cluster or sequence inserted into plant deoxyribonucleic acid (DNA), (3) a characteristic of a plant resulting from the expression of a genetic trait, or (4) reference growing practices (e.g., for organic crops or specialty crops) or preferentially (5) predicted yield based on the method disclosed herein.

In the U.S., the government (e.g., Federal Grain Inspection Service) establishes grain standards under the United States Grain Standards Act that are suitable for defining commodity grains. The detailed grain standards are currently set forth in 7 C.F.R. §810.101 through §810.2205. Under U.S. grain standards, corn is divided into three classes: yellow, white and mixed; each class may be associated with a grade ranging from U.S. No. 1 to U.S. No. 5. The grades of corn are generally based on minimum test weight per bushel, percentage of heat damage, percentage of broken kernels, and amount of foreign material. Similarly, in the U.S. for commodity soybeans the applicable soybean grades (e.g., U.S. No. 1) are generally based on test weight, heat damage, foreign material content, total damage and splits (e.g., broken seeds).

In another embodiment, the current methods may be used in conjunction with a contractual agreement. For instance, the grower may predict the yield of a crop destined to be used to make for instance a biofuel such as ethanol. In one aspect the grower could use these grain yield predictions to estimate a given amount of ethanol that might be obtained from said crop and base a contractual agreement with a ethanol producer on this information. It may be useful for example, for a grower to guarantee a certain amount of grain to be delivered to a ethanol plant prior to harvest allowing for the ethanol producer and grower to better manage supply of necessary grain to sustain a ethanol plant. Likewise, the methods disclosed herein may be useful in the production of enzymes in plants, cellulosic biofuels, or food/feed distributors.

FIG. 5 demonstrates a typical workflow using the novel yield predicting methods disclosed herein. As shown in the top box labeled "Plant Sampling", one would first sample un-pollinated maternal reproductive tissue(s) (i.e. spikelet tissue, ear shoots, etc). This sampling can be carried out any time prior to pollination and/or harvesting. For instance one may sample at anywhere between 1 to 10 weeks prior to harvesting or in some instances anywhere between 1 to 20 weeks prior to harvesting. When the crop is maize, one embodiment is to sample at the VT-R1 (tasseling to first reproductive stage in maize) phase. In one embodiment of the invention, one will sample multiple subpopulations of a crop population to gain a overall representation of the entire crop population. Population sampling can be accomplished using well known statistical sampling methods known in the art. For example see, *Choosing and Using Statistics: A Biologist Guide* by Calvin Dytham (2011); *Large Sample Methods in Statistics: An Introduction With Applications* by Pranab et. al. (1993) Following plant sampling, the process entails screening the sampled plant tissues for yield metabolites as represented in the box labeled "Yield Metabolite Profiling" of FIG. 5. In some aspects these metabolites are measured in specific tissues (e.g. unpollinated female reproductive tissue) or may be measured in any tissue or multiple plant tissues. Techniques for metabolite profiling are well known in the art. See e.g., U.S. Pat. Nos. 7,005,255; 7,329,489; 7,433,787; 7,550,258; 7,550,260; and 7,553,616 and U.S. Published Application Nos. 20020009740; 20040146853; 20050014132; 20060134676, 20060134677; 20060134678; 20070172820; 20070172885; 20010178599; 20070026389; 20070032969; 20070288174; 20070298998; 20080124752; 20080161228; 20090017464; 20090075284; 20090093971; and 20090155826 all incorporated by reference. Biomarkers of yield identified herein include molecules associated with for example nitrogen use, stress responses, or sugar pathways. Following yield metabolite profiling, the next step in the workflow as represented by FIG. 5 is "Yield Prediction". Yield prediction can be performed by associating the presence or non-presence of certain yield metabolites such as those disclosed herein with a yield value collected from historical yield data which associates the levels of yield metabolites with yield. For instance, one could a) carry out multiple subsampling of plant tissues from a crop population; b) perform yield metabolite profiling c) harvest the crop population and collect actual yield data; d) compare the yield metabolite data of b) with the actual yield data of c); e) compile a X/Y axis calibration curve to represent the comparison of d). For instance, one could chart the actual yield data on the X-axis and the yield metabolite concentrations on the Y-Axis. f) using the calibration curve of d) one could quickly profile yield metabolites from a plant sample pre-pollination and correlate a predicted yield of said plant or a plant population. It is also understood that one may measure one or more yield metabolites in a tissue and establish certain thresholds that give a predicted range of predicted yields. For example, if a theoretical yield metabolite "A" is measured at <50 ug/ul then the predicted yield would be for example 50-100 bushels per acre. Likewise, one could build upon the threshold for example >50 ug/ul of a relative yield metabolite indicates for instance 100-150 bushels per acre. The following is given just as an example and demonstrates how one could build a fast predictive method for yield. Once the yield is predicted, one may make various business decisions based on the yield prediction which is represented in FIG. 5. For instance, a grower may use the predicted field values of a given crop to plan for seed harvesting, handling, storage and transportation. In another aspect the user may be using predicted yield values to calculate a discount for items such as crop insurance coverage. The predictive methods may also be used in business decisions relative to downstream supply of processes such as biofuel (i.e. ethanol) production, production of enzymes in harvested transgenic plant parts, animal feed or food for human consumption. In another aspect the business decision may be relative to crop forecasting models and in evaluation of overall crop performance in a region which findings could be employed in future plantings (i.e. application of fertilizer, application of various insecticides or herbicides, water usage). In another aspect the business decision might be a means of selecting plant lines for yield in a plant breeding program. It is also contemplated that one may employ yield metabolites (e.g. glutamine measured in un-pollinated reproductive tissue) as yield markers in a plant breeding program. Another aspect is that the business decision may be relative to the evaluation of transgenic plants expressing a suspected gene that confers increased yield for efficacy. For instance, transgenic plants expressing a given gene or genes under evaluation for increased yield could be quickly evaluated using the yield predictive methods described herein. This method could save both money and time in the evaluation of transgenes for increased yield. In another aspect the business decision may assist the grower in entering upon contractual agreements where a certain amount of grain for instance is to be delivered at a future time point. The predictive methods described herein could help said grower to make better estimates of their likely output and allow to better shape the terms of the contract. The above are purely examples of various "business decisions" that could be carried out following the predicting yield of a crop.

EXAMPLES

The following examples have been included to illustrate modes of the invention. Certain aspects of the following examples are described in terms of techniques and procedures found or contemplated by the present co-inventors to work well in the practice of the invention. In light of the present disclosure and the general level of skill in the art, those of skill will appreciate that the following examples are intended to be exemplary only and that numerous changes, modifications, and alterations may be employed without departing from the scope of the invention.

Example 1

Plant Tissue Sampling

Four maize lines (A. B, C, and D) were selected for the study based upon the lack of close genetic relation to each other and because they had shown varied nitrogen use efficiencies in a previous year of testing. The field study was machine planted. A complete factorial in a randomized complete block design with four replications was used in which hybrid and N rate were the treatment factors. Each plot consisted of four rows, 17.5 feet in length and spaced 2.5 feet apart. A soil-applied insecticide (tefluthrin) was applied in furrow at a rate of 0.099 lb a.i. $acre_{-1}$. Weed control consisted of a pre-emergence application of Lumax (S-metolachlor+atrazine+mesotrione) at the labeled rate. N was applied as ammonium sulfate $((NH4)2SO4)$ in a diffuse band after emergence and incorporated between V2 and V3. The N treatments were applied to between and on either side of the middle two rows of each four row plot. The N rates were 0, 50, 100, 150, and 200 lbs N per acre. The density at harvest was approximately 28,000 plants per acre. Due to destructive sampling of un-pollinated earshoots in one row of each plot, this experiment was harvested by hand (one row per plot). All grain yields are reported in bushels per acre at 15.5% moisture content.

Plants' emerging earshoots at the VT-R1 (tasseling to first reproductive stage in maize) were covered with a shoot-bag and allowed to grow for 5-10 days. After 5-10 days of growth, un-pollinated female inflorescence tissue (earshoot) was collected and flash frozen in liquid nitrogen for further analysis. Three plants were sampled from each plot in four replications with a total of 12 samples from each hybrid. The three plants from each plot were pooled and analyzed as one sample to minimize plant to plant variability. A total of 80 plots (samples) were analyzed. As shown in Table 1 increased application of Nitrogen corresponded to increased yield as expected for each of the four maize lines. Delta Yield was calculated for each of the lines as shown in Table 1. Delta yield is a common comparison of the yield obtained under a nitrogen titration experiment comparing varying rates of nitrogen application. Delta Yield in Table 1 is calculated by subtracting the yield of the 0 N applied treatment (i.e. Treatment 0 lbs. N/ac) from the highest rate of N treatment (i.e. treatment 200 lbs. N/ac). As expected Delta Yield varied from line to line.

TABLE 1

| Nitrogen Rate (lbs. N/ac) | Maize Lines | | | |
|---|---|---|---|---|
| | A | B | C | D |
| 0 | 62.8 | 16.4 | 40.8 | 14.6 |
| 50 | 103.1 | 50.6 | 96.8 | 69.1 |
| 100 | 137.9 | 130.1 | 144 | 118.4 |
| 150 | 162.1 | 143 | 161.5 | 123.3 |
| 200 | 190.2 | 165 | 173.1 | 152.6 |
| Delta Yield | 127.4 | 148.6 | 132.3 | 138 |

Example 2

First Metabolic Profiling Study

Samples from Example 1 were ground to a fine powder in a modified shredder under dry ice conditions and then sent for metabolite profiling and statistical analysis. Each sample was then analyzed for 267 metabolites using methods essentially as described in Anal. Chem., 2009, 81 (16), pp 6656-6667; and herein incorporated by reference. For visualization of biochemical differences between the various treatment groups, the data are displayed in line plot format. From this analysis, several metabolites profiled in corn un-pollinated ear shoots were shown to positively correlate with yield. The metabolite glutamine measured from unpollinated ear shoots showed a high correlation to yield (approximately 0.89). Likewise, 5-oxoproline, aspartate, arginine and proline metabolite levels measured in unpollinated ear shoots also correlated to grain yield (>0.80). The table below shows the metabolites with the highest positive correlation to yield prediction.

TABLE 2

| Metabolite | Correlation with yield |
|---|---|
| glutamine | 0.8874 |
| 5-oxoproline | 0.844 |
| X-14625 (glucoside of glutamine) | 0.8335 |
| aspartate | 0.824 |
| arginine | 0.8181 |
| proline | 0.8061 |
| phosphate | 0.7425 |
| homoserine-lactone | 0.7381 |
| leucine | 0.7002 |
| asparagines | 0.6725 |

The following table shows the metabolites that are negatively correlated to yield.

TABLE 3

| Metabolite | Correlation with yield |
|---|---|
| X-12792 | −0.8659 |
| N6-acetyllysine | −0.8433 |
| succinate | −0.8179 |
| N-acetylproline | −0.799 |
| 3-methoxytyrosine | −0.796 |
| X-14738 | −0.7919 |
| s-adenosylmethionine (SAM) | −0.7819 |
| X-11713 | −0.7623 |
| X-13878 | −0.7429 |
| myo-inositol | −0.73 |

The following table measures the rate of change for each identified metabolite. The rate of change is a factor in determining correlation with grain yield.

TABLE 4

| BIOCHEMICAL NAME | Fold of Change | | | | | | | | | | | | | | | |
|---|---|---|---|---|---|---|---|---|---|---|---|---|---|---|---|---|
| | 700 | | | | 701 | | | | 702 | | | | 703 | | | |
| | 2/1 | 3/1 | 4/1 | 5/1 | 2/1 | 3/1 | 4/1 | 5/1 | 2/1 | 3/1 | 4/1 | 5/1 | 2/1 | 3/1 | 4/1 | 5/1 |
| 5-oxoproline | | | | | | | | 1.35 | | | | | | | 1.14 | |
| alanine | | 0.95 | 0.83 | 1.03 | 1.24 | | | 1.21 | 1.06 | 0.99 | 1.10 | 1.30 | 1.06 | 1.30 | 1.34 | 1.29 |
| arginine | | | | | | | | 1.16 | | | | | 1.02 | | | |
| asparagine | | 1.87 | 1.86 | | 1.59 | | | 1.17 | 1.63 | 1.92 | | 1.00 | | | | |
| aspartate | 1.31 | | | | 1.51 | | | | 1.46 | | | 1.80 | 0.94 | | | |
| cysteine | 0.94 | | 0.85 | 0.71 | 0.71 | 0.93 | 0.85 | 0.65 | 1.69 | 1.18 | 0.99 | 1.67 | 1.21 | 1.05 | 1.05 | 1.09 |
| glutamate | 1.06 | 1.19 | 1.25 | 0.97 | 0.87 | 1.08 | 0.88 | 0.85 | 1.29 | 2.24 | 1.79 | 1.23 | 0.72 | 0.79 | 0.98 | 0.89 |

TABLE 4-continued

| | | | | | | | | | | | | | | | | |
|---|---|---|---|---|---|---|---|---|---|---|---|---|---|---|---|---|
| glutamine | — | — | — | 1.58 | — | — | — | — | — | — | 1.24 | — | — | — | — | — |
| glycine | — | 0.87 | 0.85 | 1.07 | 1.09 | — | — | — | 1.07 | 1.21 | 1.29 | 1.39 | 0.79 | 1.01 | 1.02 | 1.19 |
| histidine | — | — | 1.87 | 1.37 | 1.60 | — | — | — | 1.64 | 1.70 | 1.68 | 1.45 | 1.27 | 1.42 | 1.69 | 1.23 |
| isoleucine | — | 1.70 | 1.30 | 1.18 | — | — | 1.14 | — | 1.58 | 1.59 | 1.25 | 1.40 | 1.29 | 1.01 | 1.12 | 0.86 |
| leucine | — | — | — | — | — | — | — | — | 1.36 | 1.63 | 1.38 | 1.64 | 1.23 | 1.25 | 1.41 | 1.33 |
| lysine | — | — | 1.22 | 1.56 | 1.16 | — | — | 1.37 | 1.38 | 1.24 | 1.14 | — | 0.89 | 0.93 | 1.37 | 0.89 |
| methionine | — | — | 1.19 | 1.10 | 1.15 | 1.13 | 1.25 | 0.85 | 0.88 | 1.08 | 0.91 | 1.16 | 1.11 | 0.86 | 0.99 | 0.95 |
| phenylalanine | 1.23 | 1.26 | 1.16 | 1.15 | 1.15 | 1.07 | 1.18 | 0.83 | 0.95 | 1.16 | 1.00 | 1.16 | 1.12 | 0.98 | 1.07 | 1.05 |
| proline | — | — | — | — | 1.84 | — | — | — | — | — | — | 1.30 | — | — | — | — |
| serine | 1.36 | 1.28 | 1.09 | 1.24 | — | — | 1.35 | 1.08 | 1.09 | 1.30 | — | 1.28 | 1.02 | 1.20 | 1.24 | 1.13 |
| threonine | — | — | — | 1.21 | — | 1.11 | 0.96 | — | 1.33 | — | 1.09 | 1.14 | 1.20 | 1.00 | 1.05 | 0.80 |
| tryptophan | — | 1.66 | 0.93 | 0.69 | — | 1.19 | 0.80 | 0.57 | 2.07 | 1.31 | 0.61 | 0.70 | 1.49 | 0.76 | 0.84 | — |
| tyrosine | — | 1.15 | 1.04 | 1.06 | 1.28 | 1.20 | 1.14 | 0.96 | 0.90 | 1.08 | 0.96 | 1.03 | 1.05 | 0.82 | 0.86 | 0.76 |
| valine | — | 1.69 | 1.35 | 1.48 | — | — | — | 1.36 | 1.26 | 1.49 | 1.41 | 1.47 | 1.26 | 1.29 | 1.39 | 1.20 |

The following table identifies the metabolites highly correlated with yield. The increase of amino acids observed in this study primarily resided in the main nitrogen entry points of glutamate and aspartate family of amino acids.

TABLE 5

| Metabolite | Type | Function |
|---|---|---|
| glutamine | Amino acid | Glutamate metabolism |
| aspartate | Amino acid | Alanine and aspartate metabolism |
| proline | Amino acid | Urea cycle; arginine-, proline-, metabolism |
| 5-oxoproline | Amino acid | Glutathione metabolism |
| X - 14625 (glucoside of glutamate) | Amino acid | Glutamate metabolism |
| arginine | Amino acid | Urea cycle; arginine-, proline-, metabolism |
| phosphate | Energy | Oxidative phosphorylation |
| leucine | Amino acid | Valine, leucine and isoleucine metabolism |
| homoserine lactone | Amino acid | Glycine, serine and threonine metabolism |
| asparagine | Amino acid | Alanine and aspartate metabolism |

Example 3

Re-Analysis of Metabolic Data

Data Normalization and Preprocessing:

Raw and imputed data generated in Example 2 was reanalyzed using different methods. The raw data consisted of measurements of all of the metabolites identified in the study by various chromatographic methods. The imputed data is the raw data that has been median normalized where missing values are imputed using the lowest value of a given metabolite. Either raw or imputed data was loaded into SimcaP+12™ software from Umetrics™. All of the metabolite values for the various samples were entered as "X" variables and yield and NUE data were designated "Y" variables. There were a total of 1861 (8.5%) missing values in the raw data for this study. There were no missing data points with the imputed data.

Data Analysis

Principal component analysis was performed on the raw, non-imputed data to determine the greatest sources of variance. A total of 10 significant components were detected in the data. A plot of the first and second PCs indicated that there was some separation of the samples grown in low (zero additional N) compared to the other samples. That is, there were obvious changes in metabolite abundance in plants grown in lower N compared to higher N.

To determine the co-variance of metabolite abundance in relation to yield, the algorithm OPLS (orthogonal projections to latent structures) (Johan Trygg and Svante Wold, (2002) *J. Chemometrics* 16:119-128; Johan Trygg, (2002) *J. Chemometrics* 16:283-293) was applied where metabolites were "x" variables and yield was "y" variables. OPLS is similar to PLS (also called partial least squares), however, the algorithm defines orthogonal components as systematic variance, making data interpretation easier. The algorithm defines components predictive of variance in 2 matrices X and Y, in this case metabolite abundance and yield, and defines variation in X that is orthogonal (systematic) to Y. A single significant component was obtained with the raw metabolite and yield data and 2 orthogonal components that explain variance in metabolite abundance not associated with yield. A scores plot was developed and the predictive component (X-axis) and the $2^{nd}$ orthogonal component show a clear separation of the 5 different nitrogen applications associated with increasing yield.

The resulting plot clearly indicated a gradient from left to right (the predictive component of co-variance of X and Y) of low to higher N applied to the different plots in the study. The gradient from lower to higher rates of N application also correlates well with increasing yield. A loading plot of the same components was developed. The loadings are the X variables (metabolites) that explain the variance displayed in the scores plot. In the loadings plot, the metabolites follow the same X axis, so that metabolites at the right of the axis have the lowest loadings (essentially the lowest correlation to yield) and the metabolites at the right have the highest loadings, or highest correlation to increasing yield.

These results are highly similar to the results obtained in Example 2 using more standard statistical determination of correlation. All of the ten metabolites were confirmed as being highly correlated with yield using OPLS. In addition, asparagines and putrescine were also identified as being highly correlated with yield.

In order to make a more thorough comparison to the analyses performed in Example 2, the imputed data were also analyzed using OPLS. The imputation was performed by filling in the missing values for a given metabolite with the lowest value of that metabolite across all of the samples. The data were also scaled to the median of each metabolite across all of the samples. The overall variance of the imputed data was significantly different from the raw data as indicated by principal components analysis. However, the correlation of metabolite abundance to yield using the imputed data was strikingly similar to the data obtained with the raw data. As with the raw data, OPLS identified only a single significant component predictive of metabolite abundance and higher yield. The plot generated is similar to the previous plot and shows a clear separation of samples with increasing yield values and increasing rates of N input. Thus, using either raw or imputed metabolite data, the same metabolites were identified as having higher correlation to yield, and the metabolites closely match the results obtained in Example 2 using standard statistical methods. The twelve metabolites positively correlated with yield are in the following table:

TABLE 6

| Metabolite | Type | Function |
| --- | --- | --- |
| glutamine | Amino acid | Glutamate metabolism |
| aspartate | Amino acid | Alanine and aspartate metabolism |
| proline | Amino acid | Urea cycle; arginine-, proline-, metabolism |
| 5-oxoproline | Amino acid | Glutathione metabolism |
| X - 14625 (glucoside of glutamate) | Amino acid | Glutamate metabolism |
| arginine | Amino acid | Urea cycle; arginine-, proline-, metabolism |
| phosphate | Energy | Oxidative phosphorylation |
| leucine | Amino acid | Valine, leucine and isoleucine metabolism |
| homoserine lactone | Amino acid | Glycine, serine and threonine metabolism |
| asparagine | Amino acid | Alanine and aspartate metabolism |
| putrescine | Amino acid | Polyamine metabolism |

In addition, a number of metabolites were found that were predictive of yield but had a negative correlation. The metabolites showing negative correlation are in the following table:

TABLE 7

| Metabolite | Type | Function |
| --- | --- | --- |
| 6-N-acetyllysine (6-acetamido-2-aminohexanoic acid) | Acetyl-derivation of the amino acid lysine | Epigenetics, post-translational regulation, protein metabolism |
| Succinate | Energy | Krebs cycle |
| N-acetylproline | Amino acid | Urea cycle; arginine-, proline-, metabolism |
| 3-methoxytyrosine | Derivative of the amino acid tyrosine | Protein metabolism |
| S-adenosyl-methionine (SAM) | Amino acid | Cysteine, methionine, SAM, taurine metabolism |
| Myo-inositol | Lipid | Inositol metabolism |

Four additional unknown metabolites are also negatively correlated with yield, X-12792, X-14738, X11713, and X-13878.

Example 4

Second Metabolic Profile Study

Following the general methods described in Examples 1 and 2, the global metabolic profiles in ear shoots were obtained from twenty five corn genotypes, grown under five different nitrogen regimens, zero (no added nitrogen), 56, 112, 168, 224 Kg/Hectare, were studied. Field data obtained for each of the 25 genotypes was used to find a correlation of the metabolite with yield. Consistent with the findings of Example 2, many amino acids, including nitrogen carriers asparagine and glutamine, as well as the purine metabolite allantoin, were found to show strong correlations with grain yield.

For visualization of biochemical differences between the various treatment groups, the data are displayed in line plot format. The data selected for display by line plot were filtered by statistics or included for completion of a biochemical pathway. Correlation analysis for yield was carried out using the log transformed value for each metabolite and the corresponding yield (Mg/Hectare) for individual plants. Both the entire data set and selected parts of the data set were used for this analysis. The p-value and the q-value were computed to assess the statistical significance. Greater than 125 metabolites showed a correlation with yield at a statistical significance of p=<0.05. Of these the top twenty metabolites that correlated positively with yield are shown in the table below, and twenty metabolites that correlated negatively with yield are shown in second table below.

TABLE 8

Metabolites that have a positive correlation with yield.

| Biochemical Name | p-value | q-value | CORRELATION-yield |
| --- | --- | --- | --- |
| asparagine | 0.00E+00 | 0.00E+00 | 0.5335 |
| homoserine lactone | 0.00E+00 | 0.00E+00 | 0.48 |
| proline | 0.00E+00 | 0.00E+00 | 0.4423 |
| glutamine | 0.00E+00 | 0.00E+00 | 0.437 |
| glycine | 0.00E+00 | 0.00E+00 | 0.4235 |
| arginine | 0.00E+00 | 0.00E+00 | 0.4072 |
| alanine | 0.00E+00 | 0.00E+00 | 0.3917 |
| 5-oxoproline | 0.00E+00 | 0.00E+00 | 0.3562 |
| valine | 0.00E+00 | 0.00E+00 | 0.3558 |
| serine | 0.00E+00 | 0.00E+00 | 0.3347 |
| 2-aminobutyrate | 0.00E+00 | 0.00E+00 | 0.326 |
| cyano-alanine | 0.00E+00 | 0.00E+00 | 0.3247 |
| leucine | 0.00E+00 | 0.00E+00 | 0.3045 |
| X - 14625 | 0.00E+00 | 0.00E+00 | 0.2939 |
| aspartate | 0.00E+00 | 0.00E+00 | 0.2854 |
| homoserine | 0.00E+00 | 0.00E+00 | 0.285 |
| beta-alanine | 0.00E+00 | 0.00E+00 | 0.2827 |
| allantoin | 0.00E+00 | 1.00E−06 | 0.246 |
| X - 13757 | 0.00E+00 | 1.00E−06 | 0.243 |
| ophthalmate | 0.00E+00 | 1.00E−06 | 0.2425 |

The metabolite X-14625 was confirmed to be a glucoside of glutamate. All the metabolites identified in Example 2 are also identified as positively correlated with yield, except phosphate. While any of the identified positively correlated metabolites could be used to predict yield, within the top ten metabolites with the highest correlation for both studies, glutamine, 5-oxyproline, arginine, proline, and homoserine lactone are shown to be highly correlated to yield.

TABLE 9

Top twenty metabolites that correlate negatively with yield.

| Biochemical Name | p-value | q-value | CORRELATION-yield |
| --- | --- | --- | --- |
| X - 13881 | 0.00E+00 | 0.00E+00 | −0.3517 |
| threonine | 0.00E+00 | 0.00E+00 | −0.3299 |
| X - 13878 | 0.00E+00 | 0.00E+00 | −0.3145 |
| choline phosphate | 0.00E+00 | 0.00E+00 | −0.2904 |
| Isobar: 1-kestose, levan | 0.00E+00 | 0.00E+00 | −0.2793 |
| X - 13885 | 0.00E+00 | 0.00E+00 | −0.2765 |
| N6-acetyllysine | 0.00E+00 | 0.00E+00 | −0.2731 |

TABLE 9-continued

Top twenty metabolites that correlate negatively with yield.

| Biochemical Name | p-value | q-value | CORRELATION-yield |
|---|---|---|---|
| X - 15326 | 0.00E+00 | 0.00E+00 | −0.2694 |
| X - 17815 | 0.00E+00 | 0.00E+00 | −0.2681 |
| adenosine-2',3'-cyclic monophosphate | 0.00E+00 | 0.00E+00 | −0.2495 |
| cytosine-2',3'-cyclic monophosphate | 0.00E+00 | 1.00E−06 | −0.2435 |
| X - 13130 | 0.00E+00 | 1.00E−06 | −0.2386 |
| glycerol 3-phosphate (G3P) | 1.00E−06 | 5.00E−06 | −0.2263 |
| X - 14734 | 1.00E−06 | 5.00E−06 | −0.2253 |
| guanosine-2',3'-cyclic monophosphate | 1.00E−06 | 7.00E−06 | −0.2222 |
| tryptophan | 3.00E−06 | 1.30E−05 | −0.2166 |
| X - 14752 | 3.00E−06 | 1.40E−05 | −0.2156 |
| X - 13896 | 1.10E−05 | 4.70E−05 | −0.2032 |
| X - 13046 | 1.90E−05 | 0.0001 | −0.1973 |
| 2-aminoadipate | 2.60E−05 | 0.0001 | −0.1944 |

Comparing the studies in Example 2 and Example 4, X-13878, 3-methoxytyrosine, N6-acetyllysine, and 2-aminoadipate have shown consistent negative correlation with yield.

As stated before, the results in Tables 5 and 6 are consistent with metabolites that were found to correlate with yield in Examples 1 and 2 in which 4 genotypes were tested. The main class of metabolites that correlated positively with yield were amino acids, including those involved in nitrogen storage and transport i.e. glutamine and asparagine. Small differences in the correlation coefficient between the two studies can be accounted for by a slight difference in methodology and power of the studies. In Example 2, the correlation analysis was carried out with the group mean of each metabolite, and for yield, for a particular genotype. In this Example, analysis was done on data obtained for individual samples, resulting in a higher variability. Genetic diversity of the material tested may also have contributed to the variability, as the correlations in this study were calculated with data from 25 genotypes verses 4 genotypes.

Example 5

Multivariate Modeling of Yield

Using the metabolomic data collected for Example 4 on the 25 maize genotypes grown under varying nitrogen conditions, a forward selection statistical approach was used to determine the optimum number of compounds to use to give the best prediction of yield. Forward selection starts by finding the compound which is most highly correlated with either the yield response, then searches for the next best compound which improves the prediction, and so on. It is important to note that all compounds which are highly correlated to the yield do not necessarily need to be included in the model, in that their predictive power may already be accounted for. The forward selection process is reiterated until the predictive power reaches a plateau, as determined by a cross-validation procedure. This process does not choose compounds, but only the optimum number, based on averages, that will give the best predictive power.

Once the optimum number of compounds is determined, model fitting is performed to determine a group of compounds giving good predictive power. Many models are possible, and the models shown here are only examples. The statistical program JMP® (SAS, Inc.) was used for model fitting.

The maximum predictability for yield occurs when 3 metabolites are used in combination. The three metabolites are glutamine, valine and vanillate. As can be seen in the Examples above, glutamine has a very strong correlation with yield. Valine and vanillate were not identified in the top metabolites associated with yield, as they fell into the lower 50% range. However, in the model, the different mode of action of prediction power enables valine and vanillate to augment the already strong predictive power of glutamine.

In addition, maximum predictability for yield occurs when eleven metabolites are used in combination. The eleven metabolites are homoserine lactone, threonine, adenine, aminopentanate, erythritol, nicotinate ribonucleoside, arginine, 1,3-dihydroxyacetone, lysine and methyl-2-oxopentanoate.

Although the foregoing invention has been described in some detail by way of illustration and example for purposes of clarity and understanding, it will be clear to those of skill in the art that certain changes and modifications may be practiced within the scope of the appended claims.

The invention claimed is:

1. A method of predicting yield in a plant, the method comprising;
   a) sampling un-pollinated female inflorescence tissue from a plant;
   b) measuring one or more yield metabolite markers in the tissue of a);
   c) comparing the yield metabolite markers measured in b) against a calibration curve wherein the calibration curve correlates grain yield with the yield metabolite markers measured in un-pollinated female inflorescence tissue; and
   d) predicting grain yield in a plant.

2. The method of claim 1, wherein grain yield is predicted in a unit per plant.

3. The method of claim 1, wherein the plant is a monocot.

4. The method of claim 3, wherein the plant is selected from the Poaceae family.

5. The method of claim 4, wherein the plant is selected from the group consisting of maize, rice and wheat.

6. The method of claim 1, wherein the un-pollinated female inflorescence tissue consists of any one of the following: spikelet tissue, bract tissue, spikelet meristem tissue, inflorescence stalk tissue, and immature floral tissue.

7. The method of claim 6, wherein the plant is maize and the un-pollinated female inflorescence tissue is immature floral tissue.

8. The method of claim 7, wherein the immature floral tissue is immature ear shoots.

9. The method of claim 1, wherein the yield metabolite markers are measured using the following methods HPLC, spectrophotometry, enzymatic determination or chemical analysis.

10. The method of claim 1, wherein the calibration curve correlates units per area of a grain to units per volume of one or more yield metabolite markers.

11. The method of claim 1, wherein the yield metabolite markers are positively correlated with yield.

12. The method of claim 11, wherein any one or a combination of the yield metabolite markers are selected from the group consisting of glutamine, 5-oxoproline, glucoside of glutamate, aspartate, arginine, proline, phosphate, homoserine-lactone, leucine, asparagine and putrescine.

13. The method of claim 12, wherein the yield metabolite marker is glutamine.

14. The method of claim 1, wherein the yield metabolite markers are glutamine, valine and vanillate.

15. The method of claim 1, wherein the yield metabolite markers are homoserine lactone, threonine, adenine, aminpentanoate, erythritol, nicotinate ribonucleoside, arginine, 1,3-dihydroxyacetone, isoleucylglutamate, lysine and methy-2-oxopentanoate.

16. The method of claim 1, wherein the yield metabolite markers are negatively correlated with yield.

17. The method of claim 16, wherein any one or a combination of the yield metabolite markers are selected from the group consisting of 3-methoxytyrosine, N6-acetyllysine, and 2-aminoadipate.

18. A method of predicting total grain yield of a plant population, the method comprising;
   a) sampling un-pollinated female inflorescence tissue from a subset of plants from a plant population;
   b) measuring one or more yield metabolite markers for each tissue sampled from the subset plant population of a);
   c) comparing the yield metabolite markers measured in b) against a calibration curve wherein the calibration curve correlates grain yield with the yield metabolite markers measured in un-pollinated female inflorescence tissue; and
   d) predicting total grain yield of a plant population.

19. The method of claim 18, wherein grain yield is predicted in a unit per area calculation.

20. The method of claim 18, wherein the plant population consists of monocots.

21. The method of claim 20, wherein the plant population comprises members of the Poaceae family.

22. The method of claim 21, wherein the plant population comprises plants selected from the group consisting of maize, rice and wheat.

23. The method of claim 18, wherein the un-pollinated female inflorescence tissue consists of any one of the following: spikelet tissue, bract tissue, spikelet meristem tissue, inflorescence stalk tissue, and immature floral tissue.

24. The method of claim 23, wherein the plant is maize and the un-pollinated female inflorescence tissue is immature floral tissue.

25. The method of claim 24, wherein the immature floral tissue is immature ear shoots.

26. The method of claim 18, wherein the yield metabolite markers are measured using any one of the following methods HPLC, spectrophotometry, enzymatic determination or chemical analysis.

27. The method of claim 18, wherein the calibration curve correlates units per area of a grain to units per volume of one or more yield metabolite markers.

28. The method of claim 18, wherein the yield metabolite markers are positively correlated with yield.

29. The method of claim 28, wherein any one or a combination of the yield metabolite markers are selected from the group consisting of glutamine, 5-oxoproline, glucoside of glutamate, aspartate, arginine, proline, phosphate, homoserine-lactone, leucine, asparagine and putrescine.

30. The method of claim 29, wherein the yield metabolite marker is glutamine.

31. The method of claim 18, wherein the yield metabolite markers are glutamine, valine and vanillate.

32. The method of claim 18, wherein the yield metabolite markers are homoserine lactone, threonine, adenine, aminpentanoate, erythritol, nicotinate ribonucleoside, arginine, 1,3-dihydroxyacetone, isoleucylglutamate, lysine and methy-2-oxopentanoate.

33. The method of claim 18, wherein the yield metabolite markers are negatively correlated with yield.

34. The method of claim 33, wherein any one or a combination of the yield metabolite markers are selected from the group consisting of 3-methoxytyrosine, N6-acetyllysine, and 2-aminoadipate.

35. The method of claim 18, wherein the measurements of b) are averaged and compared to the calibration curve of c).

36. A method of breeding plants to generate plant lines with higher yield, the method comprising;
   a) sampling unpollinated maternal reproductive tissue from one or more possible plant breeding candidates;
   b) measuring yield metabolite levels in the tissue of a);
   c) comparing yield metabolites levels measured in b) against a calibration curve wherein the calibration curve correlates yield with yield metabolite levels measured in unpollinated maternal reproductive tissue;
   d) predicting the yield of said one or more plant breeding candidates;
   e) selecting plant breeding partners based on the prediction in d);
   f) breeding one or more plants of e) with another plant; and
   g) generating plant lines with higher yield.

* * * * *